United States Patent
Dias et al.

(10) Patent No.: US 10,790,048 B2
(45) Date of Patent: Sep. 29, 2020

(54) PATIENT TREATMENT RECOMMENDATIONS BASED ON MEDICAL RECORDS AND EXOGENOUS INFORMATION

(71) Applicant: International Business Machines Corporation, Armonk, NY (US)

(72) Inventors: Daniel M. Dias, Mohegan Lake, NY (US); Shiva B. Kumar, Scarsdale, NY (US); Ajay Mohindra, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 360 days.

(21) Appl. No.: 15/248,271

(22) Filed: Aug. 26, 2016

(65) Prior Publication Data

US 2018/0060494 A1 Mar. 1, 2018

(51) Int. Cl.
*G16H 10/60* (2018.01)
*G16H 50/20* (2018.01)
(Continued)

(52) U.S. Cl.
CPC ............. *G16H 10/60* (2018.01); *G16H 40/63* (2018.01); *G16H 40/67* (2018.01); *G16H 50/20* (2018.01); *G16H 70/20* (2018.01)

(58) Field of Classification Search
CPC ....... G16H 10/60; G16H 50/20; G06F 19/325
(Continued)

(56) References Cited

U.S. PATENT DOCUMENTS 6,458,080 B1 * 10/2002 Brown ................ G06F 19/3481
600/300
8,670,998 B2 3/2014 Bertha et al.
(Continued)

FOREIGN PATENT DOCUMENTS

GB 2475091 A 5/2011

OTHER PUBLICATIONS

"GlucoSuccess", Massachusetts General Hospital, http://glucosuccess.org/, accessed online Jul. 21, 2016, 4 pages.
(Continued)

*Primary Examiner* — Jason S Tiedeman
*Assistant Examiner* — Rachel F Durnin
(74) *Attorney, Agent, or Firm* — Stephen J. Walden, Jr.; William J. Stock

(57) ABSTRACT

Mechanisms are provided for implementing a patient health management system. The mechanisms analyze a patient electronic medical record (EMR) for an identified patient to identify a medical condition associated with the patient and identify, based on the results of the analysis, one or more exogenous data parameters associated with the medical condition. The exogenous data parameters are parameters specifying conditions outside the patient's body that affect the health of the patient with regard to the medical condition. The mechanisms retrieve exogenous data, corresponding to the exogenous data parameters, from one or more exogenous data sources and generate a health management plan for the patient based on the exogenous data. The health management plan comprises actions to be performed or not performed by the patient to thereby minimize effects of exogenous conditions, corresponding to the exogenous data parameters, on the health of the patient with regard to the medical condition.

18 Claims, 6 Drawing Sheets

(51) Int. Cl.
  *G16H 70/20* (2018.01)
  *G16H 40/67* (2018.01)
  *G16H 40/63* (2018.01)

(58) Field of Classification Search
  USPC .......................................................... 705/2–3
  See application file for complete search history.

(56) References Cited

U.S. PATENT DOCUMENTS

| | | | |
|---|---|---|---|
| 9,144,381 B2 | 9/2015 | Rosen | |
| 2008/0306763 A1* | 12/2008 | James | G16H 50/30 705/2 |
| 2009/0254378 A1* | 10/2009 | Janas, III | G06F 19/325 705/3 |
| 2012/0084092 A1* | 4/2012 | Kozuch | G06Q 50/22 705/2 |
| 2012/0165617 A1 | 6/2012 | Vesto et al. | |
| 2012/0220835 A1 | 8/2012 | Chung | |
| 2014/0006047 A1* | 1/2014 | Amathnadu | G16H 10/60 705/2 |
| 2014/0081659 A1* | 3/2014 | Nawana | G16Z 99/00 705/3 |
| 2015/0066172 A1* | 3/2015 | Yi | G16H 20/30 700/91 |
| 2015/0294086 A1* | 10/2015 | Kare | G06F 19/3481 705/3 |
| 2016/0103966 A1 | 4/2016 | Mirza | |
| 2017/0017776 A1* | 1/2017 | Soulos | G06F 19/3475 |
| 2017/0039344 A1* | 2/2017 | Bitran | G06F 19/3475 |
| 2017/0177822 A1* | 6/2017 | Fogel | G16H 50/30 |
| 2017/0308666 A1* | 10/2017 | Thomson | G06F 19/3418 |

OTHER PUBLICATIONS

"ResearchKit and CareKit", Apple Inc., http://www.apple.com/researchkit/, accessed online Jul. 21, 2016, 14 pages.

"Situational Awareness and Risk Management in Healthcare", Status Solutions, http://www.statussolutions.com/markets-served/acute-care, accessed online Jul. 21, 2016, 5 pages.

LV, Ziyu et al., "iCare: A Mobile Health Monitoring System for the Elderly", 2010 IEEE/ACM International Conference on Green Computing and Communications (GreenCom) and International Conference on Cyber, Physical and Social Computing (CPSCom), Dec. 18-20, 2010, 7 pages.

Mell, Peter et al., "The NIST Definition of Cloud Computing", National Institute of Standards and Technology, Information Technology Laboratory, Version 15, Oct. 7, 2009, 2 pages.

Ren, Yonglin et al., "Monitoring Patients via a Secure and Mobile Healthcare System", IEEE Wireless Communications, Feb. 2010, pp. 59-65.

Shahriyar, Rifat et al., "Intelligent Mobile Health Monitoring System (IMHMS)", Lecture Notes of the Institute for Computer Sciences, Social Informatics and Telecommunications Engineering (LNICST 27), 2010, 8 pages.

Shu, Lei et al., "Poster Abstract: Integrating Weather Information with Body Sensor Networks for Health Monitoring", Proceedings of the 6th International Conference on Body Area Networks (BodyNets'11), Nov. 7-10, 2011, pp. 124-125.

* cited by examiner

PATIENT TREATMENT RECOMMENDATIONS BASED ON MEDICAL RECORDS AND EXOGENOUS INFORMATION

BACKGROUND

The present application relates generally to an improved data processing apparatus and method and more specifically to mechanisms for providing medical treatment recommendations for patients based on both the patient's electronic medical records and other exogenous information.

Monitoring patients with chronic illnesses, such as congestive heart failure, diabetes, and asthma represents one of the greatest challenges facing modern medicine. Patients with chronic illnesses require ongoing, follow-up treatment and care to properly manage their conditions. Unfortunately, a number of these patients do not receive ongoing treatment and care, receive treatment and care on a sporadic basis, or receive treatment and care which is not in accordance with recommended guidelines. Worse, patients often fail to do the basic simple day-to-day tasks that could prevent or reduce the frequency and magnitude of a catastrophic event such as a hospitalization. As a result, these patients often unnecessarily suffer from symptoms of their chronic illness which would have been minimized or prevented with proper ongoing treatment and care. Additionally, some of these patients may later require hospitalization, or in severe cases some of these patients may die, both of which may have been prevented if the patient was receiving the proper ongoing treatment and care.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a patient health management system. The method implemented by the patient health management system comprises analyzing a patient electronic medical record (EMR) for an identified patient to identify a medical condition associated with the patient and identifying, based on the results of the analysis, one or more exogenous data parameters associated with the medical condition. The exogenous data parameters are parameters specifying conditions outside the patient's body that affect the health of the patient with regard to the medical condition. The method further comprises retrieving exogenous data, corresponding to the exogenous data parameters, from one or more exogenous data sources and generating a health management plan for the patient based on the exogenous data. The health management plan comprises actions to be performed or not performed by the patient to thereby minimize effects of exogenous conditions, corresponding to the exogenous data parameters, on the health of the patient with regard to the medical condition.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
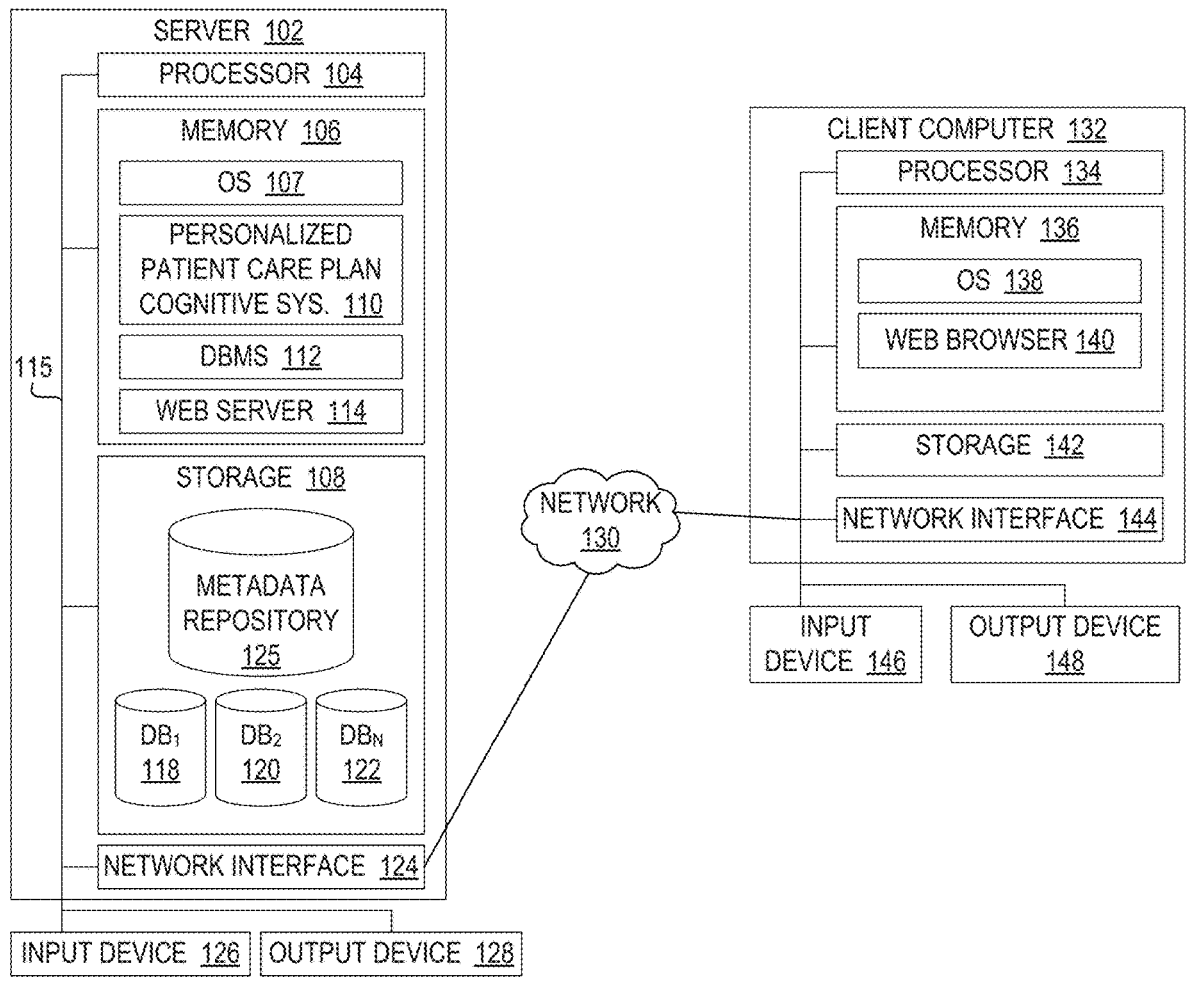
FIG. 1 is a block diagram illustrating a cloud computing system 100 for providing software as a service, where a server provides applications and stores data for multiple clients in databases according to one example embodiment of the invention.

In addition to the problems associated with monitoring the chronic illness of patients and helping patients perform the day-to-day tasks to control their chronic illness, many medical diagnosis and treatment recommendation and monitoring systems operate based only on information in the electronic medical records (EMRs) of the patient. Such systems do not take into account exogenous information, such as environmental conditions, e.g., weather conditions, allergen level information, pollution levels, or other factors existing outside the patient's body that may affect a patient's chronic medical conditions. Such conditions may change dynamically and thus, the treatment of the chronic medical condition may change from one time period to another or from one geographical location to another, e.g., a patient living in Dallas, Tex. and having a particular chronic medical condition may require different treatment than another patient with the same chronic medical condition living in a different geographic location, such as San Jose, Calif.

The illustrative embodiments provide mechanisms for obtaining information from one or more exogenous information sources and evaluating the information in conjunction with other electronic medical records (EMRs) of a patient to determine a best treatment recommendation for a patient's medical condition, where this treatment recommendation may comprise a personalized patient care plan that specifies actions or activities to be performed by the patient and optionally an assessor that assesses the patient's performance of the actions or activities. The personalized patient care plan (PCP) may further specify what patient data, health parameters, and the like, are to be monitored. In some cases, based on the particular medical condition of the patient, these elements of the personalized PCP may be at least partially dependent, or affected, by one or more exogenous conditions, such as predicted or current weather, pollution, allergen levels, or other exogenous conditions. Such exogenous conditions are noted as part of the personalized PCP as parameters to be monitored and potential triggers for dynamically modifying or adjusting the personalized PCP based on an evaluation of current or predicted exogenous conditions, as may be determined from exogenous information obtained from one or more exogenous information sources. The mechanisms of the illustrative embodiments may monitor such exogenous conditions and updated activities or actions, to be performed by the patient and/or assessor, in the personalized PCP based on the current or predicted exogenous conditions and the corresponding treatment guidelines for the particular medical conditions of the patient. The personalized PCP may be dynamically modified and the modified personalized PCP may be communicated to the patient via a personal computing device. The modified personalized PCP may also be communicated to a monitoring or assessor system for automatic modification of monitoring actions, or notification to a human assessor.

In accordance with the illustrative embodiments, these exogenous information sources may include environmental condition information sources. Other exogenous data that can be used to make daily health decisions includes nutrition (sugar, fat) data, exercise data (heart rate, pulse, weight, blood pressure, blood sugar), sleep data, travel data, and the like. The exogenous data in some illustrative embodiments is any data that is non-clinical data. Thus, exogenous data can include patient monitored information such as exercise, sleep, specific activities such as walking gait, tremble picking up a weight, measurements before and after events like a meal, etc. The exogenous data can also include calendar items such as planned travel, where a very busy schedule may be correlated with sleep data, for example. The exogenous data may also comprise Internet of Things (IoT) data such as items consumed/retrieved from a refrigerator, and the like.

The exogenous data comes from various exogenous information sources which may include various types of source including, but not limited to, web sites, information pushing systems, newsfeed websites and systems, or any other system that collects exogenous condition data and makes it available to other computing systems, either on a public domain or commercial basis. For example, the website arinow.gov provides an air quality index map, the website weather.com provides detailed weather information and commuter weather information, and veronet.eu is another website that provides traffic and pollution prediction information. Other websites may be used to provide exogenous data such as nutritional websites providing caloric, fat, sugar content, etc. for various food items. While these websites exist and may be used as sources of exogenous information, accessing these sites is presently done through a manual process on an individual basis. The mechanisms of the illustrative embodiments use information communication interfaces, which may comprise application programming interfaces (APIs) or other logic for interfacing with such exogenous information sources to obtain such exogenous information, determine what exogenous information is pertinent to a particular patient's personalized PCP, and then evaluating the exogenous information relative to treatment guidelines for the patient's personal medical condition(s) to determine if modifications to the patient's personalized PCP should be made. If such modifications are to be performed, then the modifications are made and the modified personalized PCP is sent to the patient and optionally to an assessor.

For example, patient data, including patient identification and demographic information, diagnosis information, lab test information, history and other data is extracted from an electronic medical record (EMR) and demographic source and stored in an EMR extract data structure. Knowledge data and patient care plan guidelines, which may include various sources of medical knowledge, official medical treatment guidelines, position papers, and the like, for a variety of medical maladies, such as chronic diseases, are extracted from patient care plan guidelines and knowledge sources and stored in a knowledge summary and guidelines data structure. The patient or a care manager, such as a physician or other medical personnel, a patient assessor, or the like, initiates a process through a patient health management system specifying a request to generate a personalized PCP using a patient identifier to identify the patient for which the personalized PCP is to be generated. The patient health management system implements cognitive system logic for analyzing the gathered information from the EMRs, demographic information, diagnosis information, lab test information, history information, medical guidelines and knowledge information, etc. and generates a personalized PCP for the specified patient including any conditional exogenous data parameters that need to be monitored and may trigger dynamic modification of the personalized PCP. The conditional exogenous data parameters to be monitored are specific to the medical conditions of the patient and may be identified based on the medical guidelines and knowledge as applied to the personal information about the patient as provided in the patient's EMRs, demographic information, diagnosis information, lab test information, history information, etc.

For example, under high pollution levels, a patient with asthma may have their personalized PCP dynamically modified, and corresponding notifications may be generated and output to the patient, indicating that the patient should minimize strenuous activity, such as outdoor exercise. The patient may access the patient health management system via the patient's associated mobile device or personal computing device to obtain the patient's personalized PCP which configures the patient's personal patient systems, e.g., applications on a mobile device, health/activity monitoring device, and the like, to implement the personalized PCP. The mobile device, health/activity monitoring device(s), and the like, may monitor the patient with regard to the personalized PCP, and pushes this information to one or more assessor systems, which operate in conjunction with the patient health management system, which assess the patient's current conditions, adherence to the patient's PCP, and the like, and provides monitoring results to the patient health management system.

In addition, data from exogenous information sources, such as weather/environment websites and other data sources, is pulled or pushed to the patient health management system. Based on this information, the patient health management system performs analysis to determine current and/or predicted exogenous conditions for the patients whose health is being managed by the patient health management system. The patient health management system then analyzes each of the personalized PCPs of the patients that are being managed and determines which personalized PCPs are affected by the current and/or predicted exogenous conditions. Such a determination may be made based on the exogenous parameters for monitoring specified in the personalized PCPs and determining if a changed exogenous condition as determined through the analysis matches an exogenous parameter condition specified in the personalized PCP, e.g., specific allergen levels above a predetermined threshold, a pollution level above a specified threshold level, etc. For those personalized PCPs that are affected by the determined current and/or predicted exogenous conditions, the personalized PCPs are modified in accordance with medical guidelines and treatment knowledge so as to avoid unnecessary risks to the patient's health. The modified personalized PCP may then be pushed to the patient's systems and/or assessor systems and appropriate notifications output to the patient and/or assessor indicating a change in the personalized PCP based on the current and/or predicted exogenous conditions. Such operations may be performed on a continuous or periodic basis, or in response to a triggering event, such as a patient or assessor request, receipt of a pushed environmental condition warning from an official exogenous information source, e.g., environmental condition warning from a government website or exogenous information source, or the like.

It should be appreciated that the modified personalized PCP may be stored in conjunction with an identifier of the patient as a temporarily modified personalized PCP that is in effect until the patient health management system determines that the current and/or predicted exogenous condition triggering the modification has subsided and the patient's health management may return to a normal state. Thus, both the original personalized PCP and the modified personalized PCP may be stored in association with the patient with one being made active over the other depending on the particular exogenous conditions determined to currently exist or predicted to exist. In this way, multiple personalized PCPs may be generated that are keyed to different exogenous conditions and may be associated with different exogenous conditions such that if the exogenous condition occurs again in the future, the already stored modified personalized PCP may be automatically selected without having to rebuild the modified personalized PCP each time that the exogenous condition is determined to occur. Hence, multiple personalized PCPs for different exogenous conditions may be built up over time.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In the following description, reference is made to embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

In addition, it should be appreciated that the present description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, providing treatment and care for patients having illness requiring ongoing treatment is a major issue in modern medicine. Many times this ongoing treatment and care is a shared responsibility between the medical workers, e.g., doctors, nurses, etc. and the patient. That is, the patient must perform certain actions on their own to provide selftreatment for the illness, which often involves making different lifestyle choices, e.g., changing diet, increasing physical activity, taking prescribed medications, eliminating habits and consumption of products that are detrimental to health, etc., with the medical workers providing monitoring and periodic checks of the patient's progress to ensure that the patient is adhering to the treatment needed to control and/or improve the patient's condition.

A number of mechanisms have been developed for assisting the patient and medical workers in handling their shared responsibilities including mechanisms for generating patient care plans based on the patient's medical condition, mechanisms for patient's to self-monitor their adherence to their own care plans, and the like. Such mechanisms often regard patients as generic types of patients, e.g., a generic asthma patient, a generic diabetes patient, etc. possibly with some classification within these generic categories based on the patient's age, gender, race, and other generic demographics. Even with such classification within the generic categories, the resulting care plan associated with the patient is one that is applicable to multiple patients having the same set of medical diagnosis and demographics. The care plan is not in fact personalized to the specific patient but to a general categorization of the patient.

Each individual patient has a specific and different set of lifestyle conditions that make that patient unique from other patients. It is this uniqueness that is not reflected in the patient care plans generated by known mechanisms. That is, the known patient care plan mechanisms are created to classify patients into generic categories and apply generic care plans to these patients. While mechanisms employing such patient care plan mechanisms may refer to them as being "personalized" or "customized" to the patient, they in fact are only superficially customized in that they may be customized based on generic customization categories, e.g., customized based on generic demographics such as age, race, gender, etc. As a result, patients are not in fact presented with a patient care plan that the patient feels is specifically suited to them. The patient care plans do not in fact take into account the patient's own individual circumstances and can be applied to a plurality of patients having the same demographics and medical condition, e.g., all 40 year old female diabetes patients. There are no mechanisms that personalize a patient's on-going treatment and care based on both their medical condition and the patient's own personal lifestyle, taking into account multiple lifestyle conditions and the facilities and resources available to that particular patient based on their lifestyle.

It should be appreciated that the term "lifestyle" as it is used herein refers to the way in which a person lives their lives. The term "lifestyle information" refers to the data collected that characterizes the lifestyle of the patient and may encompass various temporal, spatial, environmental, and behavioral information/data about the patient that together comprises a unique combination of information/ data that characterizes and represents the way in which that specific patient conducts their life on a daily basis. The lifestyle information for a patient is specific to that patient and is not generally applicable to multiple patients. The lifestyle information may be provided at various levels of granularity depending upon the particular implementation. As part of this lifestyle information, data generated by the specific patient via one or more computing devices or other data communication devices may be included such as actions performed by the patient on a daily basis, personal schedules, specifications of preferences, etc. For example, lifestyle information may include the patient entering information, such as into a computing device executing a patient tracking application, indicating that the patient ate breakfast at a fast food restaurant in the airport on the way to Virginia this morning. In addition, data generated by external systems associated with third parties that characterizes the patient's lifestyle may be included in the lifestyle information as well, e.g., a healthcare insurance company may have information about the patient's lifestyle, e.g., smoker, overweight, sedentary, high risk for diabetes, etc., which may be characteristic of the patient's lifestyle.

For example, with regard to temporal lifestyle information, the lifestyle information may comprise one or more data structures specifying one or more schedules of events that the patient undergoes either on a routine basis or on a dynamic basis, e.g., a baseline routine schedule that may be dynamically updated as events occur or do not occur. The temporal lifestyle information may comprise, for example, the time that the patient wakes in the morning, when they have their meals, when they go to work and return home, when they take their children to school, when they shop for groceries, when they go to bed at night, scheduled non-routine events, free time, scheduled flight, ferry, train, or other ground transportation departure/arrival times, and/or any other temporal information characteristic of the patient's daily life and other non-routine scheduled events.

With regard to spatial lifestyle information, this information may comprise one or more data structures identifying locations associated with the patient's daily lifestyle including routine locations frequented by the patient, e.g., the location of their home, the location of their work, the location of their child's school, the location of the retail establishments that they frequent, the location of their doctors, the typical travel paths between locations utilized by the patient, and the like. The spatial lifestyle information may further comprise information about each location including the number of stories or levels in the buildings, e.g., two-story home, five-story office building, etc., whether the location has stairs, etc. The spatial lifestyle information may further comprise geographic information including the city, state, county, country, etc., in which the patient lives, works, travels to, or otherwise conducts their life.

With regard to environmental lifestyle information, this information comprises one or more data structures with indications of the environmental quality and resource availability in the environments in which the patient is present, is predicted to be present at a later time (such as based on the temporal and spatial lifestyle information), or typically is present on a daily or routine basis. For example, environmental lifestyle information may include information about the patient's home location, e.g., in a rural, urban, or suburban environment, has access to parks, walking trails, etc. This environmental lifestyle information may include information about the patient's work location including whether the patient works in an office setting with fluorescent lights and relative quiet, in a manufacturing setting with heavy machinery and loud noises, works with computers the majority of the day, has his/her own office or is in a cubicle, the number of co-workers the patient has that they interface with on a daily basis, the types and/or identities of establishments around the patient's home/work for purposes of determining access to resources (e.g., products and services), air quality, weather conditions, elevation (for purposes of oxygen level determination, for example), and the like.

Regarding behavioral lifestyle information, this information comprises one or more data structures having indications of the patient's own behavior and likes/dislikes, i.e.

lifestyle preferences. The behavioral lifestyle information may comprise such information as the patient's habits, responses to communications of different modalities, patterns of activity, and the like. For example, such behavioral lifestyle information may indicate that the patient has a habit of eating a snack every evening after 9 p.m. or takes his/her dog for a walk in the mornings before 9 a.m. and after 5 p.m. The behavioral lifestyle information may further indicate the patient's likes and dislikes (preferences) with regard to various elements of daily life including types of foods the patient likes/dislikes, types of physical activity the patient likes/dislikes, when the patient likes to engage in certain activities, e.g., exercising before work/after work, or the like.

The various lifestyle information data may be obtained directly from the patient, such as via an electronic questionnaire, through analysis of electronic medical records (EMRs) or other entries in databases associated with the patient (e.g., governmental databases associated with a patient's social security number, address, or the like), or otherwise obtained from one or more monitoring devices and/or applications utilized on one or more computing devices associated with the patient and with which the patient interacts, e.g., patient tracking applications on a smart phone, a medical monitoring device, or the like, that monitors physical activity, food logs, and the like. The lifestyle information is utilized to customize or personalize a patient care plan for the specific patient such that the patient is presented with a resulting patient care plan that the patient feels is tailored specifically to them and the way they conduct their lives.

In addition to known patient care plan mechanism suffering from the drawback of not in fact generating personalized patient care plans taking into account a patient's unique lifestyle, the known patient care plan mechanisms also do not provide for the ability to integrate third-party information about the lifestyle of a patient into the patient care plan personalization such that a more complete understanding of the capabilities of the patient based on their lifestyle is realized when generating and monitoring the patient's adherence to the patient care plan. For example, third-party lifestyle information may comprise information from commercial and governmental computing systems, databases, and the like, that characterize the patient's environment, availability to resources (e.g., products/services/facilities), etc., or is otherwise ancillary and further defining of other lifestyle information associated with the patient.

As one example, a third-party lifestyle information source may comprise a global positioning system (GPS) source that identifies the patient's associated locations, e.g., home, work, etc., and identifies establishments around those locations that provide resources that are of interest to the patient's lifestyle and potentially of interest in generating a patient care plan. For example, specialty grocery stores, vitamin stores, pharmacies, restaurants, gyms, walking paths, parks, recreational areas, community pools, and the like, may be identified based on a GPS system and its associated databases of information. This information may include identifications of types (e.g., Vietnamese Restaurant) and specific identities (e.g., "ABC Pho") of the particular establishments which can be used with other third-party lifestyle information sources (e.g., "ABC Pho" website comprising menu and nutrition information) to retrieve specific information about those identified establishments. For example, a particular restaurant may be determined to be within a specified distance of the patient's home location and corresponding restaurant menu item information and hours of operation information may be retrieved from that particular restaurant's website, computing system, or other database. The retrieved menu item information and hours of operation information may be used, as described hereafter, to correlate the information with patient care plan information, e.g., nutritional and caloric information may be correlated with the patient care plan, to generate patient care plan actions/tasks and/or recommendations for assisting the patient in adhering to the patient's personalized patient care plan. Similarly, other third-party lifestyle information sources may provide information for correlation with patient care plan actions/tasks including hours of operations, products/services provided, distance from the patient's locations, and the like.

Exogenous information is information representing potentially dynamically changing conditions outside the patient's body which may affect the health condition of the patient. Whereas lifestyle information is more static in nature and is used to generate the core personalized patient care plan (PCP) for the patient, the exogenous information is used as a basis for modifying the core personalized PCP to dynamically adjust for the dynamically changing, or predicted, exogenous conditions. Thus, examples of exogenous information include weather condition information, pollution level information, allergen level information, and the like. Other exogenous data that can be used to make changes to the PCP include nutrition (sugar, fat), exercise information (heart rate, pulse, weight, blood pressure, blood sugar), sleep and other patient monitored information. Yet other exogenous data include monitoring of specific activity such as walking gait, or hand writing or tremble, data from a patient calendar information, such as planned travel, data from Internet of Things (IoT) devices, such as a smart refrigerator providing data on foods removed, etc.

The illustrative embodiments of the present invention collect patient demographic and medical data, such as from questionnaires, electronic medical records (EMRs), lab test results, hospital records, insurance company records, governmental agency reports, and the like, and generate a baseline patient care plan based on an initial diagnosis of the patient's medical condition, one or more categorizations of the patient based on the collected demographic and medical data, established patient care plan guidelines and knowledge, such as from official medical diagnosis and treatment guidelines and knowledge sources, and goals to be achieved by the patient care plan. Thus, for example, a patient's demographic information and electronic medical records may indicate that the patient is a 40 year old female that has been diagnosed with diabetes. Various pre-established categories and sub-categories may be defined for different types of patients in an ontology based on the various demographic and medical history characteristics, e.g., a category for diabetes patients, a sub-category of patients in the age range of 40 to 50 years old, a sub-sub-category of female patients, and so on.

Similarly, medical treatment guidelines may be established for defining ways in which to treat various medical maladies with these treatment guidelines having various triggering patient characteristics. For example, a medical treatment guideline may specify that for female diabetes patients that are in the age range of 40 to 60 years old, the patient should follow a low sugar diet and have at least 30 minutes of stressful exercise per day. A database of such treatments and their guidelines may be provided that correlates various combinations of patient characteristics with a corresponding treatment. Thus, by categorizing the patient in accordance with their characteristic information as obtained from demographic and medical data for the patient, these categories may be used to evaluate the applicability of the various treatments by matching the categories with the patient characteristics of the treatments to identify the best treatment for the patient, i.e. the treatment having the most matches between the patient categories and the treatment's required patient characteristics.

At this point, a general patient care plan is generated for the patient that identifies the treatment, which may be an on-going treatment, which should be prescribed for the patient. A patient care plan in this context is essentially a set of goals and actions for achieving those goals. As will be described hereafter, in addition, the present invention includes, in a patient care plan, a patient monitoring plan with specific actions to be taken on the part of an assessor to monitor and interface with the patient to elicit positive results from the patient, e.g., adherence to the patient care plan.

While a general patient care plan is present at this point, the general patient care plan has not yet been personalized or customized to the specific patient's unique lifestyle information. That is, while in general a 40 year old female diabetes patient should follow a low sugar diet with 30 minutes of stressful exercise each day, not every patient's lifestyle will accommodate such actions in the same way.

The illustrative embodiments may further operate to personalize the general patient care plan to the particular lifestyle of the specific patient. Lifestyle information data is obtained from various sources to obtain an overall representation of the lifestyle of the patient. Examples of such sources include geospatial information sources, commercial establishment websites or computing devices/databases, governmental or regulatory organization information sources, and the like. These third-party lifestyle information sources may provide lifestyle information that is combined with lifestyle information provided by the patient himself/herself for analysis to identify the types of personalized care plan actions to be used with the patient's care plan, the timing of the actions, and the types and timing of patient care plan monitoring and management actions to be performed by an assessor, e.g., a human assessor, automated assessment system, or a combination of human and automated assessment mechanisms. Thus, the selection of patient care plan actions (i.e. patient actions and monitoring actions) is based on the general patient care plan goals, the general patient care plan actions to be performed, and the personalization of these general patient care plan actions to the specific lifestyle of the patient.

Various lifestyle information analysis logic is provided to evaluate and classify the patient's lifestyle in accordance with a number of defined lifestyle categories. For example, the patient's lifestyle may be categorized according to level of physical activity, level of availability to healthy food sources, quality of home and work environment (lighting, air quality, quietness, safety, etc.), level of access to exercise facilities, various qualitative aspects of the patient's home and work life, and the like. From these categories, a more specific patient care plan is generated to achieve the goals and actions of the generic patient care plan, e.g., prescribe a specific type of diet plan which the patient has access to foods that meet with the diet plan and has a schedule that facilitates preparation of particular types of food.

For example, if the patient has limited time due to long work hours, having young children that require attention in the mornings/evenings before/after work, and the like, then food preparation time will be determined to be a minimum and thus, a corresponding diet plan will be selected for this particular type of lifestyle involving more processed foods than another patient that may have more time to perform more complex food preparation actions. Similarly, based on the patient's lifestyle information as obtained from the various sources, the mechanisms of the illustrative embodiments may prescribe a walking regimen based on the fact that the patient lives near a walking trail (as obtained from GPS data) and works in a building that has multiple floors (as obtained from patient supplied lifestyle information, GPS data, and/or governmental real estate databases) such that walking the stairs is an option. The patient's lifestyle information may further indicate an ability to prescribe a strength-building regimen since the patient lives near a gym (obtained from GPS data) or has gym facilities at their office (obtained from the patient supplied lifestyle information and/or real estate database information listing amenities of the building where the patient works). The timing of such actions may be specified in the patient care plan such that the walking regimen may instruct the patient to take a 25 minute walk at 8 a.m. every weekday and walk up/down the stairs at their office on their way to and from work and to and from lunch. The patient care plan may further specify that the patient is to go to the gym on Tuesday and Thursday at 7:30 p.m. to do 30 minutes of strength building exercise.

The granularity of the patient care plan may be even more specific depending upon the implementation. For example, with regard to a walking regimen, a particular path for the patient to walk may be specified in order to achieve a desired level of stress on the patient may be specified based on the geospatial information for the patient's home, work, and other locations, e.g., "Walk up Main Street to $2^{nd}$ Street, take a left, walk along $2^{nd}$ Street to Picard Street, take a left, walk down Picard Street to $1^{st}$ Street, take a left, and return to building." Such a path determination may be made based on information obtained about the geographical location of the patient's office building including the elevations of the streets to indicate uphill or downhill walking, distances, etc.

Because the lifestyle information may comprise specific establishment information, the patient care plan actions may be further personalized to the patient's particular locations and may specify particular establishments that can be frequented as well as what products/services the patient can utilize to be in compliance with the patient's prescribed care plan. For example, the menu items at a local restaurant may be analyzed to identify which menu items meet the diet requirements of the patient's care plan, e.g., low sugar foods, and the restaurant and its compliant menu items may be provided to the patient as part of their patient care plan. Personal trainer information for gyms may be obtained which includes the personal trainers' schedules, class schedules, and times of availability such that the patient may be instructed, as part of their personal patient care plan, when would be the best time for them to go to the gym to obtain personal trainer assistance with their strength building exercise regimen.

This more personalized patient care plan may further be customized to the specific lifestyle of the patient by evaluating the temporal lifestyle information and behavioral lifestyle information for the patient. Thus, having established a set of goals and actions to achieve those goals that are specific to the patient based on their demographics, medical data, and the patient's lifestyle information, the goals and actions may be converted to specific actions to be taken by the patient on a daily basis. For example, the patient's lifestyle information may be further analyzed to identify specific exercise actions to be taken by the patient based on their location, the facilities available, the patient's personal schedule of activities during the day, the patient's personal likes/dislikes (preferences), etc. For example, the patient may have a schedule that shows that the patient is available to exercise between 8 and 9 a.m. and 7:00 p.m. till 8:00 p.m. on most weekdays, is not available Thursday evenings after work for exercise, is available between 1 and 2 p.m. on Saturdays, and all day on Sundays. The preferences may further state that the patient does not like hot or rainy weather. The patient lifestyle information may further indicate that the patient likes to sleep late on Saturdays and Sundays and thus, while available early on these days, the mechanisms of the illustrative embodiments may adjust the scheduling of actions in the personalized care plan to accommodate this timing preference of the patient.

It can be appreciated that because the lifestyle information that may be utilized to provide personalization of patient care plans is varied and vast, the types of personalizations that may be made to a patient care plan are likewise varied and vast. The patient care plan personalization mechanism of the illustrative embodiments provides logic for analyzing and evaluating a large set of lifestyle information data from various sources, determine specific patient care plan actions that meet the categorization and characterization of the patient's lifestyle as obtained from the analysis of the patient's lifestyle information, as well as achieves the goals and general actions associated with the generalized patient care plan corresponding to the patient's demographics and medical data, and compose the various personalized patient care plan actions into a series of actions to be taken by the patient over a set time period, e.g., daily, weekly, monthly, etc., in order to achieve desired goals of the patient care plan.

Thus, the illustrative embodiments provide various mechanisms for providing actual personalized patient care plans based not only on a categorization of the patient based on their medical diagnosis and demographic information, but also based on their own specific lifestyle information and lifestyle information obtained from third-party sources, e.g., information sources that provide information about a user's geographical surroundings, establishments in the user's geographical surroundings, event information sources, and the like. By personalizing the patient's care plan to their specific lifestyle, the likelihood that the patient will adhere to the care plan and perform the actions specified in the care plan is increased. Essentially, the personalized patient care plan helps to instruct the patient how the patient can integrate the care plan into their existing lifestyle without placing the burden on the patient to perform the analysis and evaluation on how to achieve such integration.

Having generated a personalized patient care plan taking into account the patient's personal lifestyle, the illustrative embodiments further provide mechanism for assisting and controlling the monitoring of a patient's adherence to the personalized care plan as well as assist health professionals, assessors, automated assessment systems, and the like, in performing actions and initiating communications to maintain ongoing treatment and care of the patient. Such mechanisms may involve evaluating the lifestyle information for the patient, the personalized care plan with its associated care plan actions, and determining appropriate monitoring actions/communications to be performed, timing of monitoring actions/communications, communication modes to be utilized, content of such communications, and the like, so as to maximize a positive response from the patient. Examples of such monitoring actions may be interrogating health monitoring devices and/or applications associated with the patient, e.g., wearable devices such as a FitBit™, pedometer, GPS device, applications running on a patient's smart phone or other computing device, or the like, initiating a reminder communication to be sent to the patient to remind them to perform an action in accordance with their personalized patient care plan, scheduling a doctor's appointment for the patient and informing them of the appointment, initiating a call to the patient's telephone to discuss their progress, or any other action that a human or automated assessment system may perform to assist with the monitoring of the patient's adherence to the patients' personalized patient care plan.

The particular monitoring actions to be employed are matched to the specific personalized patient care plan that is associated with the patient. That is, for each patient care plan action, there may be a set of one or more possible monitoring actions that may be associated with that type of patient care plan action. Selection from amongst the one or more possible monitoring actions may be performed based on an analysis of the patient's lifestyle information to determine the most appropriate monitoring action that will not interfere with the patient's lifestyle and will most likely result in a positive response from the patient. For example, if it is determined that the patient's lifestyle is such that the patient eats breakfast at 8:30 a.m. and one of the patient care plan actions is to eat oatmeal for breakfast three times a week, then a monitoring action may be selected that involves texting the patient with a message at 8:25 a.m., with the message having content that states "consider eating oatmeal for breakfast today." Other options may be to call the patient or send an electronic mail message but the patient's lifestyle information indicates that the patient is not a "morning person" and thus, is unlikely to respond well to calls in the morning and is generally in a rush to go to work since the patient eats breakfast at 8:30 a.m. and needs to be at the office by 9:30 a.m. indicating little time for checking electronic mail.

As with the personalized patient care plan, the monitoring plan and its monitoring actions, as well as their timing, may be personalized to the personalized patient care plan and the specific patient's lifestyle information. For example, if the patient works in a manufacturing environment where noise levels are high, it is unlikely that the patient will want to conduct a telephone conversation with a human assessor and is more likely to be responsive to textual communications. Thus, during working hours, monitoring actions may be restricted to textual communications, such as instant messaging or electronic mail. Similarly, if the patient works in a hospital, school, or other location where disturbances are to be minimized, communications may not be made during times of the day where the patient is likely to be present in such locations. Furthermore, as another example, if it is known that this particular patient weighs himself and takes his blood sugar measurements each morning at approximately 9:00 a.m., then a monitoring action may be to send a request to the electronic scale and/or blood sugar analysis mechanism to request the results of that day's measurements. Thus, monitoring plans and corresponding monitoring actions are selected based on the patient's personalized patient care plan, the patient actions specified in the personalized patient care plan, and the lifestyle information for the particular patient.

In an even further aspect of the illustrative embodiments, the generation of the personalized care plan, and thus, the patient actions and monitoring actions of an assessor, may further take into consideration historical analysis of both the present patient and other similar patients with regard to previously prescribed patient care plans associated with these patients and their relative success/failure at adhering to these previously prescribed patient care plans and/or individual patient care plan actions that are part of these previously prescribed patient care plans. That is, historical analysis of patient information is performed across multiple patients to determine which care plans patients previously were able to adhere to, which care plans, and individual patient actions or tasks within patient care plans, resulted in successful outcomes for the patients, which resulted in unsuccessful outcomes for the patients, and generates a prediction as to the best patient care plans, patient actions or tasks, etc. to be given to future patients having similar attributes. This will result in patient care plans having tasks/actions for both the patient and the assessor that are tailored to the particular patient, as mentioned above, but in which previous success of other similar patients is taken into account when generating the personalized patient care plan. This historical analysis can be performed in the aggregate over a plurality of patients and/or on an individual basis based on what this particular patient has shown success, or lack thereof, with in the past.

For example, if it is determined that diabetic patients that are female, in the age range of 40-45, and are smokers tend to have negative results when their patient care plan involves strong cardiac exercise for 30 minutes a day (i.e., the patient tends to fail to complete this task), then future prescribed patient care plans may adjust based on this historical analysis. For example, the future patient care plans may reduce the requirement or substitute the requirement of the care plan, e.g., replace the patient action with one that requires mild cardiac exercise for 30 minutes a day. Alternatively, if it determined that diabetic patients that are female, in the age range of 40-45, and are smokers tend have positive results when their patient care plan involves drinking coffee and eating oatmeal for breakfast, then this may be added to future care plans for similar patients. Thus, adjustment of future patient care plans is made based on historical analysis of similar patient care plans and the patient's own history indicating positive results and adherence to previous patient care plans, e.g., if this particular patient has a history of failing to perform stressful exercise based patient actions in the past, then future patient care plans for this patient may be modified to not include stressful exercised based patient actions.

It should be appreciated that this historical evaluation may be performed at any point during the process of personalizing a patient care plan as previously described above. Thus, for example, in one illustrative embodiment, the historical analysis may be performed when generating the generalized patient care plan so as to identify the general goals and corresponding general patient care plan actions that previously have been most likely achieved by the current and other patients. In addition, either in the same or other illustrative embodiments, the historical analysis may be performed when personalizing the generic patient care plans based on the patient's lifestyle information. That is, historical analysis may be performed based on the patient's previous personalized patient care plans to determine what types of physical exercise actions the patient has previously been able to adhere to, which they have not been able to adhere to, or the like.

In cases where similar patient care plan actions have not been previously prescribed for this patient, patient care plan information for similar patients, such as in a cohort of patients having similar demographics and medical data, may be analyzed to identify the patient actions that similar patients have been able to adhere to and utilize those as a basis for generating personalized patient actions in the personalized patient care plan for the present patient. Such actions may be personalized to the current patient's lifestyle in the manner previously described above. For example, assume that the general patient care plan calls for 30 minutes of stressful exercise which the patient has not been previously prescribed to perform, but similar patients have been able to adhere to 30 minutes of brisk walking a day and thus, this patient action is used as a basis for generating the present patient's general patient care plan. This action may then be personalized to the particular patient's lifestyle by generating specific personalized patient care plan actions for performing brisk walking at 8:00 a.m., along Hyde Street, for 25 minutes and then 5 minutes of stair walking at work on weekdays due to the patient working in a multi-story building.

In yet a further aspect of the illustrative embodiments, mechanisms are provided for dynamically adjusting or modifying personalized patient care plans based on a determined level of adherence to the personalized patient care plan, as determined from the monitoring actions performed and discussed above. That is, the patient's adherence to their personalized patient care plan is monitored and determinations are made as to whether the patient meets the goals set forth in the personalized patient care plan and/or performs the patient actions in the personalized patient care plan. If the patient does not meet the requirements of one or more goals in the patient care plan, an alternative goal determination logic is employed to determine an alternative goal that the patient is more likely to be able to accomplish. This determination may be made based on the patient's actual progress towards attaining the original goal, the importance and type of the goal to the overall personalized patient care plan, e.g., adjustments to medication may not be able to be made depending on the particular care plan, and a predetermined inter-changeability of the goals. In some cases, one goal may be adjusted in one direction, or by a first adjustment metric, and another in a different direction, or by a second adjustment metric, so as to balance the patient's ability to achieve a missed goal with an alternative goal while maintaining overall results that are to be generated, e.g., physical activity goal may be reduced while dietary goals may be increased so that the balance achieves the same overall effect. In this way, the patient's personalized patient care plan is further optimized for the particular patient based on the achievability of the goals for that particular patient.

In addition to finding alternative goals for a personalized patient care plan, alternative patient actions, and thus corresponding monitoring actions, may be identified for patient actions in the patient care plan that the patient has not been able to adhere to. In some illustrative embodiments, the determination of alternative care plan actions for performing the alternative goals may be based on a historical analysis of patient actions in other patient care plans that the patient and/or similar patients have undergone. This historical analysis may identify other similar patient actions that achieved similar results to the patient actions that the patient is found to not be able to achieve in the patient's current personalized patient care plan.

In addition to the personalization of a patient care plan (PCP) as described above, it should be appreciated that the creation of the personalized PCP may comprise identifying, for the particular medical maladies, medical diagnosis, or medical conditions associated with the patient, one or more exogenous parameters that affect treatment of the medical condition, diagnosis, or the like. For example, if the patient is diagnosed with an asthma condition and a weight condition, then pollution levels and allergen levels may be determined to be exogenous parameters that may affect the personalized PCP of the patient due to the asthma condition. That is, in accordance with the medical diagnosis of the patient, and the correlation of the medical diagnosis with medical treatment guidelines and knowledge, certain exogenous parameters may be associated with the patient.

As discussed above, the mechanisms of the illustrative embodiments monitor, by pulling information from, or having information pushed from, exogenous information sources and determine which patient's personalized PCPs are affected by the exogenous information based on an analysis of the exogenous information to determine a current and/or predicted exogenous condition. For those personalized PCPs affected by the exogenous condition, appropriate modifications of the personalized PCP, such as by replacing actions or activities to be performed by the patient and/or assessor with other actions or activities that minimize the impact of the exogenous condition, may be made. Thus, for example, the patient's core personalized PCP may indicate that the patient is to take a vigorous walk each day along an outdoor path. However, depending on the allergen levels and pollution levels of the patient's environment, modifications to the patient's personalized PCP may be required to avoid unnecessary risks to the patient's health. For example, rather than taking the vigorous walk each day along the outdoor path, the activity may be modified to walking on a treadmill at the gym or at home in an inside location, thereby minimizing the impact of the exogenous condition of increased allergen levels and pollution levels on the health of the patient.

Thus, in general, as can be seen from the above description and examples, the mechanisms of the illustrative embodiments combine information about a patient's medical condition, medical history, lifestyle information, geographical location(s), facilities located in these geographical locations(s), products and services available in these geographical location(s), desired goals of the care plan, and other lifestyle information, and personalizes the patient care plan to the patient's particular medical condition, particular lifestyle, and available facilities and resources to provide a specific personalized patient care plan for this specific patient that is not widely applicable to generalized categories of patients. Moreover, the core personalized PCP generated in this manner may be dynamically modified by the monitoring of exogenous information sources for changes in exogenous conditions that may affect the core personalized PCP. A modified personalized PCP may then be generated and associated with the patient, with the modified personalized PCP being sent to the patient's system(s) along with appropriate notifications of the modifications.

This information may further be used to personalize the assessment activities to be performed by the assessment system/personnel and influence the timing, communication modes, and monitoring actions performed. That is, based on the particular care plan goals and care plan actions that are part of the patient's care plan, these goals/actions may be paired with monitoring actions to be taken by an assessor, e.g., a medical professional, other individual whose duty it is to monitor and interface with patients to ensure that they are following a prescribed care plan, or automated system. The monitoring actions may likewise be personalized based on the patient's lifestyle information, geographical information, available products and services in the patient's geographical area(s) of interest (e.g., home, work, etc.), and the like. The assessment tasks may be automatically or semi-automatically performed so as to gather information for monitoring the patient's adherence to the personalized patient care plan and either automatically or semi-automatically adjust the personalized patient care plan accordingly, send notifications to the patient, notify the doctor, or perform some other desired actions for maximizing the probability that the patient will maintain adherence to the personalized patient care plan.

As noted above, the personalized patient care plans (PCPs), and the personalized PCP actions (patient actions performed by the patient and monitoring actions performed by the assessor), may be dynamically adjusted based on the patient's current environmental conditions or other exogenous condition information, changes in schedule, determined deviations from the care plan, and other dynamic conditions that may interfere or otherwise require modification, either temporarily or permanently, of the patient's personalized PCP. As noted above, such factors as weather conditions, pollution levels, allergen levels, temperature conditions, resource availability (e.g., gym is closed), and the like may require temporary modifications to a patient's personalized PCP. Other factors, such as the patient moving to a new location, obtaining a new place of employment, or the like, may require more permanent modifications to the patient's personalized patient care plan. Such factors may be identified and corresponding modifications initiated taking into account the new temporary/permanent lifestyle and exogenous condition changes.

From the above general overview of the mechanisms of the illustrative embodiments, it is clear that the illustrative embodiments are implemented in a computing system environment and thus, the present invention may be implemented as a data processing system, a method implemented in a data processing system, and/or a computer program product that, when executed by one or more processors of one or more computing devices, causes the processor(s) to perform operations as described herein with regard to one or more of the illustrative embodiments. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in the figures, and described hereafter, one or more computing devices comprising a distributed data processing system, may be specifically configured to implement a personalized patient care plan system in accordance with one or more of the illustrative embodiments. The configuring of the computing device(s) may comprise the providing of application specific hardware, firmware, or the like to facilitate the performance of the operations and generation of the outputs described herein with regard to the illustrative embodiments. The configuring of the computing device(s) may also, or alternatively, comprise the providing of software applications stored in one or more storage devices and loaded into memory of a computing device for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of one or more of the illustrative embodiments and is not a general purpose computing device. Moreover, as described hereafter, the implementation of the mechanisms of the illustrative embodiments improves the functionality of the computing device(s) and provides a useful and concrete result that facilitates creation, monitoring, and adjusting personalized patient care plans based on personalized lifestyle information and assessment of patient adherence to the personalized patient care plan.

As mentioned above, the mechanisms of the illustrative embodiments may be implemented in many different types of data processing systems, both stand-alone and distributed. Some illustrative embodiments implement the mechanisms described herein in a cloud computing environment. It should be understood in advance that although a detailed description on cloud computing is included herein, implementation of the teachings recited herein are not limited to a cloud computing environment. Rather, embodiments of the present invention are capable of being implemented in conjunction with any other type of computing environment now known or later developed. For convenience, the Detailed Description includes the following definitions which have been derived from the "Draft NIST Working Definition of Cloud Computing" by Peter Mell and Tim Grance, dated Oct. 7, 2009.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Characteristics of a cloud model are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service models of a cloud model are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment models of a cloud model are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes. A node in a cloud computing network is a computing device, including, but not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. A cloud computing node is capable of being implemented and/or performing any of the functionality set forth hereinabove.

FIG. 1 is a block diagram illustrating a cloud computing system 100 for providing software as a service, where a server provides applications and stores data for multiple clients in databases according to one example embodiment of the invention. The networked system 100 includes a server 102 and a client computer 132. The server 102 and client 132 are connected to each other via a network 130, and may be connected to other computers via the network 130. In general, the network 130 may be a telecommunications network and/or a wide area network (WAN). In a particular embodiment, the network 130 is the Internet.

The server 102 generally includes a processor 104 connected via a bus 115 to a memory 106, a network interface device 124, a storage 108, an input device 126, and an output device 128. The server 102 is generally under the control of an operating system 107. Examples of operating systems include UNIX, versions of the Microsoft Windows™ operating system, and distributions of the Linux™ operating system. More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single identity, it should be understood that the memory 106 may comprise a plurality of modules, and that the memory 106 may exist at multiple levels, from high speed registers and caches to lower speed but larger DRAM chips. The network interface device 124 may be any type of network communications device allowing the server 102 to communicate with other computers via the network 130.

The storage 108 may be a persistent storage device. Although the storage 108 is shown as a single unit, the storage 108 may be a combination of fixed and/or removable storage devices, such as fixed disc drives, solid state drives, floppy disc drives, tape drives, removable memory cards or optical storage. The memory 106 and the storage 108 may be part of one virtual address space spanning multiple primary and secondary storage devices.

As shown, the storage 108 of the server contains a plurality of databases. In this particular drawing, four databases are shown, although any number of databases may be stored in the storage 108 of server 102. Storage 108 is shown as containing databases numbered 118, 120, and 122, each corresponding to different types of patient related data, e.g., electronic medical records (EMRs) and demographic information, lifestyle information, treatment guidelines, personalized patient care plans, and the like, for facilitating the operations of the illustrative embodiments with regard to personalized patient care plan creation, monitoring, and modification. Storage 108 is also shown containing metadata repository 125, which stores identification information, pointers, system policies, and any other relevant information that describes the data stored in the various databases and facilitates processing and accessing the databases.

The input device 126 may be any device for providing input to the server 102. For example, a keyboard and/or a mouse may be used. The output device 128 may be any device for providing output to a user of the server 102. For example, the output device 108 may be any conventional display screen or set of speakers. Although shown separately from the input device 126, the output device 128 and input device 126 may be combined. For example, a display screen with an integrated touch-screen may be used.

As shown, the memory 106 of the server 102 includes a personalized patient care plan cognitive system 110 configured to provide a plurality of services to users via the network 130. As shown, the memory 106 of server 102 also contains a database management system (DBMS) 112 configured to manage a plurality of databases contained in the storage 108 of the server 102. The memory 106 of server 102 also contains a web server 114, which performs traditional web service functions, and may also provide application server functions (e.g. a J2EE application server) as runtime environments for different applications, such as the multi-tenant application 110.

As shown, client computer 132 contains a processor 134, memory 136, operating system 138, storage 142, network interface 144, input device 146, and output device 148, according to an embodiment of the invention. The description and functionality of these components is the same as the equivalent components described in reference to server 102. As shown, the memory 136 of client computer 132 also contains web browser 140, which is used to access services provided by server 102 in some embodiments.

The particular description in FIG. 1 is for illustrative purposes only and it should be understood that the invention is not limited to specific described embodiments, and any combination is contemplated to implement and practice the invention. Although FIG. 1 depicts a single server 102, embodiments of the invention contemplate any number of servers for providing the services and functionality described herein. Furthermore, although depicted together in server 102 in FIG. 1, the services and functions of the personalized patient care plan cognitive system 110 may be housed in separate physical servers, or separate virtual servers within the same server. The personalized patient care plan cognitive system 110, in some embodiments, may be deployed in multiple instances in a computing cluster. As is known to those of ordinary skill in the art, the modules performing their respective functions for the personalized patient care plan cognitive system 110 may be housed in the same server, on different servers, or any combination thereof. The items in storage, such as metadata repository 125, databases 118, 120, and 122, may also be stored in the same server, on different servers, or in any combination thereof, and may also reside on the same or different servers as the application modules.

Figure 2:
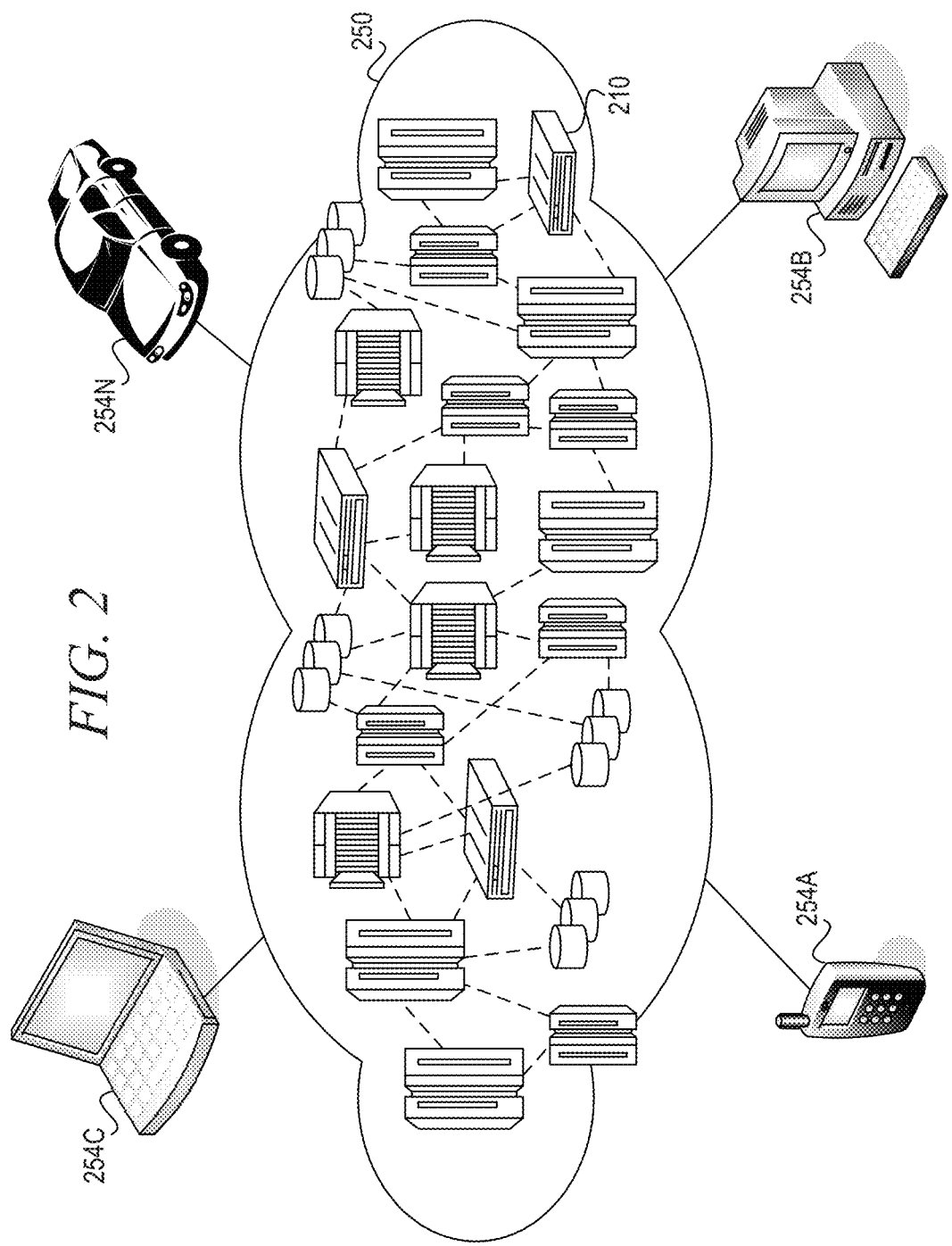
FIG. 2 is another perspective of an illustrative cloud computing environment in which aspects of the illustrative embodiments may be implemented.

Referring now to FIG. 2, another perspective of an illustrative cloud computing environment 250 is depicted. As shown, cloud computing environment 250 comprises one or more cloud computing nodes 210, which may include servers such as server 102 in FIG. 1, with which local computing devices used by cloud consumers, such as, for example, personal digital assistant (PDA) or cellular telephone 2254A, desktop computer 2254B, laptop computer 2254D, and/or automobile computer system 2254N may communicate. Nodes 210 may communicate with one another. A computing node 210 may have the same attributes as server 102 and client computer 132, each of which may be computing nodes 210 in a cloud computing environment. They may be grouped (not shown) physically or virtually, in one or more networks, such as Private, Community, Public, or Hybrid clouds as described hereinabove, or a combination thereof. This allows cloud computing environment 250 to offer infrastructure, platforms and/or software as services for which a cloud consumer does not need to maintain resources on a local computing device. It is understood that the types of computing devices 2254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
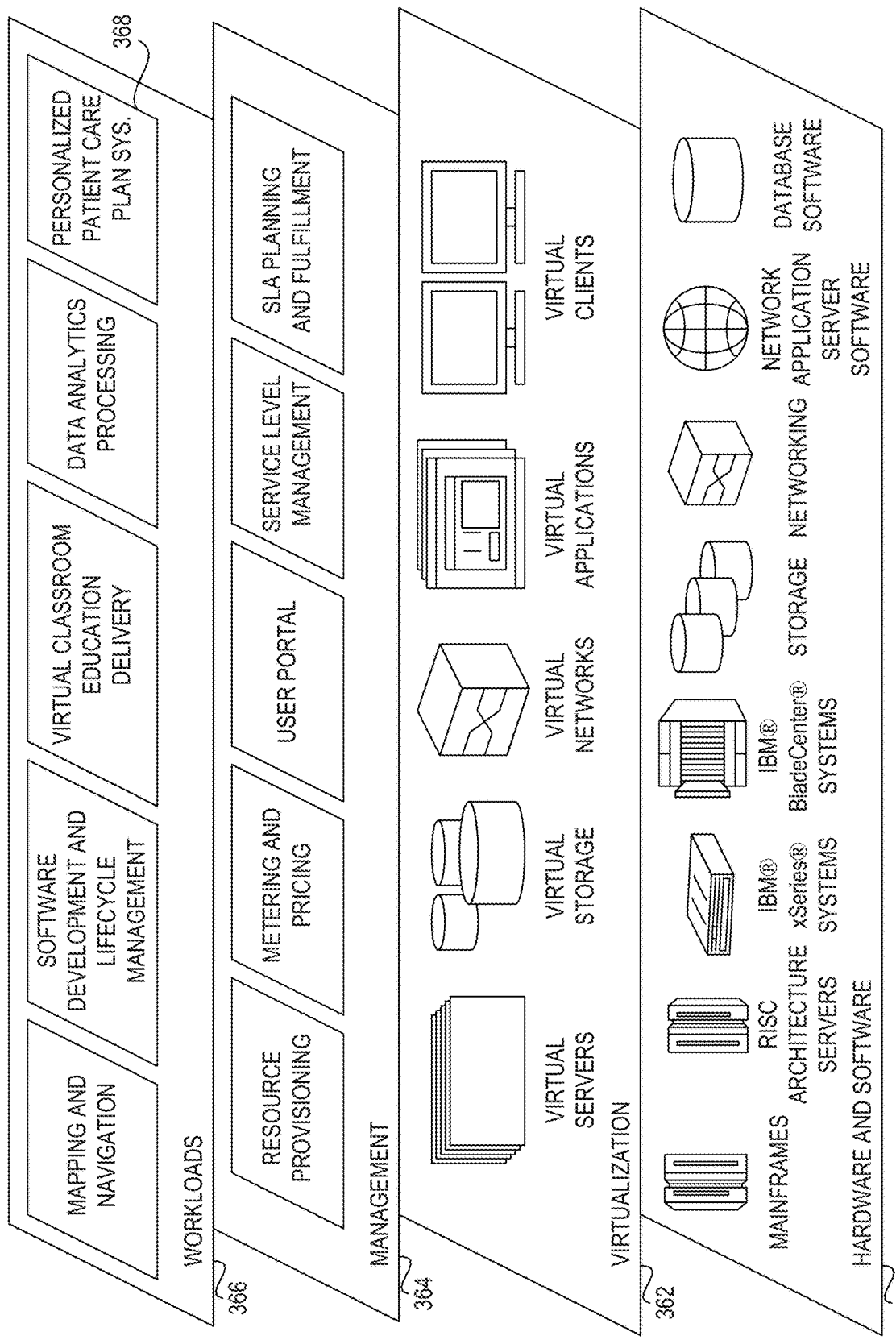
FIG. 3 is an example diagram illustrating a set of functional abstraction layers provided by a cloud computing environment in accordance with one illustrative embodiment.

Referring now to FIG. 3, a set of functional abstraction layers provided by cloud computing environment 250 (FIG. 2) is shown. It should be understood in advance that the components, layers, and functions shown in FIG. 3 are intended to be illustrative only and embodiments of the invention are not limited thereto. As depicted, the following layers and corresponding functions are provided.

The hardware and software layer 360 includes hardware and software components. Examples of hardware components include mainframes, in one example IBM™ zSeries™ systems; RISC (Reduced Instruction Set Computer) architecture based servers, in one example IBM pSeries™ systems; IBM xSeries™ systems; IBM BladeCenter™ systems; storage devices; networks and networking components. Examples of software components include network application server software, in one example IBM Web Sphere™ application server software; and database software, in one example IBM DB2™ database software. (IBM, zSeries, pSeries, xSeries, BladeCenter, WebSphere, and DB2 are trademarks of International Business Machines Corporation registered in many jurisdictions worldwide.).

The virtualization layer 362 provides an abstraction layer from which the following examples of virtual entities may be provided: virtual servers; virtual storage; virtual networks, including virtual private networks; virtual applications and operating systems; and virtual clients. In one example, management layer 364 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 366 provides examples of functionality for which the cloud computing environment may be utilized. Examples of workloads and functions which may be provided from this layer include: mapping and navigation; software development and lifecycle management; virtual classroom education delivery; data analytics processing; transaction processing; and, in accordance with the mechanisms of the illustrative embodiments, a personalized patient care plan creation, monitoring, and modification functionality, as generally represented by personalized patient care plan system 368 in FIG. 3.

Figure 4:
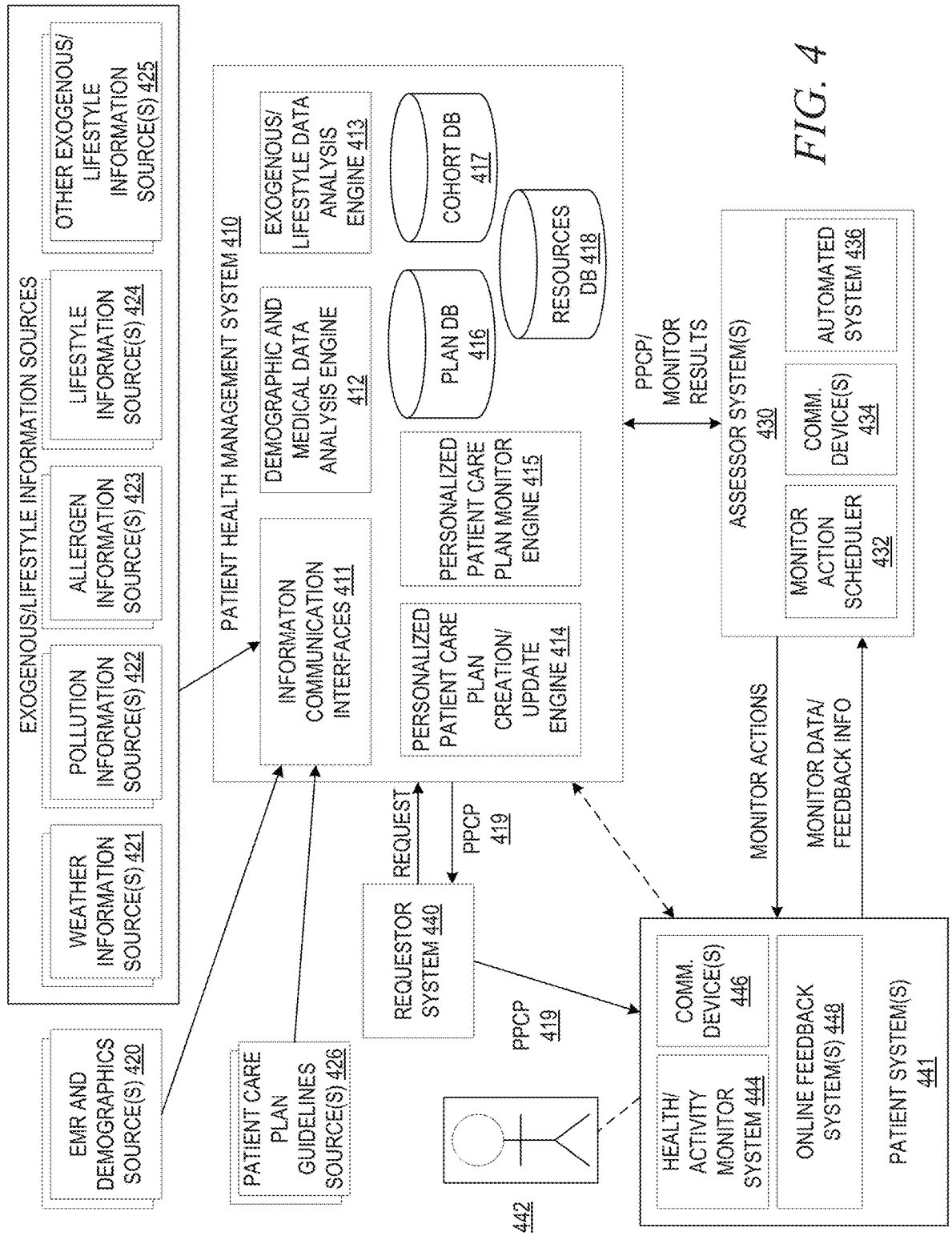
FIG. 4 is an example block diagram illustrating the primary operational elements of a personalized patient care plan creation and monitoring system in accordance with one illustrative embodiment.

As discussed above, the illustrative embodiments provide a personalized patient care plan (PCP) creation, monitoring, and modification system which may be implemented in various types of data processing systems to not only generate a personalized PCP, but also dynamically modify the core personalized PCP based on changes to lifestyle and exogenous conditions that affect the patient's medical treatment. FIG. 4 is an example block diagram illustrating the primary operational elements of such a personalized patient care plan creation and monitoring system in accordance with one illustrative embodiment. The operational elements shown in FIG. 4 may be implemented as specialized hardware elements, software executing on hardware elements, or any combination of specialized hardware elements and software executing on hardware elements without departing from the spirit and scope of the present invention.

As shown in FIG. 4, a patient health management system 410 comprises information source interfaces 411, demographic and medical data analysis engine 412, exogenous/lifestyle data analysis engine 413, personalized care plan creation/update engine 414, and personalized care plan monitor engine 415. The various elements of the patient health management system 410 may be implemented as part of a cognitive system. A cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:
  Navigate the complexities of human language and understanding
  Ingest and process vast amounts of structured and unstructured data
  Generate and evaluate hypothesis
  Weigh and evaluate responses that are based only on relevant evidence
  Provide situation-specific advice, insights, and guidance
  Improve knowledge and learn with each iteration and interaction through machine learning processes
  Enable decision making at the point of impact (contextual guidance)
  Scale in proportion to the task
  Extend and magnify human expertise and cognition
  Identify resonating, human-like attributes and traits from natural language
  Deduce various language specific or agnostic attributes from natural language
  High degree of relevant recollection from data points (images, text, voice) (memorization and recall)
  Predict and sense with situational awareness that mimic human cognition based on experiences
  Answer questions based on natural language and specific evidence In one aspect, cognitive systems provide mechanisms for answering questions posed to these cognitive systems using a Question Answering pipeline or system (QA system). The QA pipeline or system is an artificial intelligence application executing on data processing hardware that answers questions pertaining to a given subject-matter domain presented in natural language. The questions may not be posed as questions, but may be provided as requests for a cognitive system operation, e.g., a request for preparation of a personalized patient care plan for a specified patient, e.g., specifying a unique patient identifier, which may be interpreted as a question, e.g., a request of "generate personalized patient care plan for patient P" may be interpreted as "What is a personalized patient care plan for patient P?"

The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain. In the depicted example, the documentation input to the cognitive system may comprise the various inputs from sources 420-426 as well as monitored data from patient systems 441 and/or assessor systems 430.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

The QA pipeline receives the input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

In addition, the patient health management system 410 maintains a personalized patient care plan database 416 that stores data corresponding to the personalized patient care plans, and modified patient care plans, generated for various patients and a patient cohort database 417 that stores cohort association information for various patients having similar characteristics, e.g., demographics and/or medical data. Entries in the personalized patient care plan database 416 may be associated with entries in the patient cohort database 417 and may be associated with particular patients, such as by way of unique patient identifiers.

A personalization resources storage 418 provides resources utilized by the personalized care plan creation/update engine 414 for identifying and correlating demographic, medical, lifestyle information, and general patient care plan information associated with a patient into a series of personalized patient care plan actions and corresponding monitor actions for an assessor. The personalization resources storage 418 may comprise systems of rules, patterns, equations, algorithms, and various other types of logic that codify or otherwise implement functions for selecting and deciding how to personalize a general set of goals and actions in a general patient care plan to a personalized patient care plan and/or modify existing goals and actions in a personalized patient care plan based on determined levels of adherence of the patient to the patient's personalized patient care plan, current and/or predicted exogenous conditions, and the like. These rules, patterns, equations, algorithms, and the like, may be developed over time by subject matter experts. The rules, patterns, equations, algorithms, etc., may be applied to the large set of demographic, medical, and lifestyle information obtained for the patient to obtain an automatically generated personalized patient care plan which may then be presented to a subject matter expert, such as a doctor, nurse, other medical professional, or the like, for confirmation before prescribing the personalized patient care plan to the patient. It should be appreciated that the resources 418 may further be utilized by the personalized care plan monitor engine 415 when monitoring adherence to a personalized patient care plan and determining modifications to the personalize patient care plan based on determined levels of adherence and/or current/predicted exogenous conditions, as discussed hereafter.

The information source interfaces 411 provides a data communication interface through which patient data may be obtained from various sources including electronic medical records (EMRs) data source 420 and various exogenous and lifestyle information sources 421-425. As shown in FIG. 4, these exogenous/lifestyle information sources may comprise weather information source(s) 421, pollution information source(s) 422, allergen information source(s) 423, lifestyle information source(s) 424, and other exogenous/lifestyle information source(s) 425. The lifestyle information source(s) 424 may comprise various types of lifestyle information as previously noted above, such as patient supplied lifestyle information, temporal lifestyle information, spatial lifestyle information, geographical lifestyle information, and the like. Moreover, the interfaces 411 comprise interfaces for obtaining patient care plan guidelines information from source 426 which may comprise medical treatment guidelines, position paper data structures, medical expert knowledge databases and data structures, or the like.

The EMR data source 420 may comprise various sources of electronic medical records including individual doctor medical practice systems, hospital computing systems, medical lab computing systems, personal patient devices for monitoring health of the patient, dietary information, and/or activity information of the patient, or any other source of medical data that represents a particular patient's current and historical medical condition. The EMR data source 420 may further comprise data representing the patient demographics since such information is typically gathered by providers of such medical data. The EMR data source 420 provides medical information about patients to the patient health management system 410 which may be used along with the patient care plan guidelines from sources 426 and lifestyle information from sources 424, 425 to generate a core personalized patient care plan (PCP). Moreover this core personalized PCP may be modified as needed to adjust for exogenous conditions, as identified or predicted based on the exogenous information from sources 421-423 and 425, determined to affect the core personalized PCP.

The lifestyle information sources 424, 425 may be provided as a database and/or computing system that gathers and stores information from the patient indicating the patient's response to questionnaires, presented either physically and then entered through a data entry process or presented electronically and gathered automatically, directed to the patient's lifestyle, preferences, and the like. For example, questions in the questionnaire may ask questions about the patient's personal daily schedule, home and work environment conditions, family information, preferences regarding food types, exercise types, times of the day for performing actions, and the like. This information is gathered directly from the patient but may not cover all aspects of the patient's lifestyle.

This lifestyle information may be augmented by other lifestyle information gathered from other sources which may be third-party lifestyle information sources. These third-party lifestyle information may comprise information from commercial and governmental computing systems, databases, and the like, that characterize the patient's environment, availability to resources (e.g., products/services/facilities), etc. For example, third-party lifestyle information sources may comprise environment lifestyle information sources, geospatial lifestyle information sources, establishment lifestyle information sources, and other various lifestyle information data sources.

Examples of such third-party geospatial lifestyle information sources may comprise a global positioning system (GPS) source that identifies the patient's associated locations, e.g., home, work, etc., and identifies establishments around those locations that provide resources that are of interest to the patient's lifestyle and potentially of interest in generating a patient care plan. For example, as mentioned above, specialty grocery stores, vitamin stores, pharmacies, restaurants, gyms, walking paths, parks, recreational areas, community pools, and the like, may be identified based on a GPS system and its associated databases of information. Other examples of third-party lifestyle information may comprise geospatial information which may be used to request or lookup establishment information in establishment lifestyle information source(s). For example, if the geospatial lifestyle information source identifies an establishment type and specific identity of a particular establishment, this information may be used to request or lookup other third-party lifestyle information for the establishment in the establishment lifestyle information source, e.g., the establishment's website, an industry based website, blogs, commercial establishment information repository, or the like, to retrieve specific information about the identified establishment, e.g., menu items, nutrition information, hours of operation, and the like. Similarly, other third-party lifestyle information source 425 may provide information for correlation with patient care plan actions/tasks including hours of operations, products/services provided, distance from the patient's locations, and the like.

Various types of exogenous information sources 421-423 and 425 may be provided from which exogenous information is obtained, either through a pull or push process. Examples of exogenous information sources include weather information source(s) 421 which provide measures of weather conditions both currently and predicted, pollution information source(s) 422 such as air quality information services that provide current or predicted measures of pollution levels for one or more different pollutants, and allergen information source(s) 423 that provide information about current or predicted allergen levels in the air of a geographical area for one or more different types of allergens. The other exogenous information source(s) 425 may comprise information sources for other types of information characterizing exogenous conditions near the patient, such as other measures of the quality of air in a geographical area, traffic information services, crime information services, governmental information services regarding public utilities, or any other exogenous information source.

The patient care plan guidelines source 426 provides information regarding the preferred treatments for various medical conditions or maladies in association with patient characteristics. These guidelines are generally associated with demographic and medical information about patients and provide general guidelines as to who qualifies for a treatment, or patient care plan, and who does not based on their medical information and demographic information. The patient care plan guidelines provide an initial basis for determining a general patient care plan for a patient which may then be personalized to the particular patient based on the lifestyle information specific to that particular patient.

The patient health management system 410 may receive a request to generate a personalized patient care plan for a particular patient, such as from a physician's computing system, a patient computing system, or the like, which initiates the processes of the patient health management system 410 including retrieving information about the specified patient from the EMR sources 420. The EMR sources 420 provide patient demographic and medical data, gathered from questionnaires, electronic medical records, and the like, to the medical data analysis engine 412 which analyzes the received data and extracts the necessary data for generating patient care plan from the demographic and medical data received. This information is then used as a basis for submitting a request to the patient care plan guidelines source 426 to retrieve patient care plan guidelines for the patient's specific demographics and medical data, e.g., the patient is a 40 year old female diagnosed with type 2 diabetes and thus, corresponding patient care plan guidelines for this combination of patient demographics and medical condition are retrieved from the patient care plan guidelines source 426.

The retrieved patient care plan guidelines are used along with the demographics and medical data for the patient to generate a baseline patient care plan based on an initial diagnosis of the patient's medical condition, one or more categorizations of the patient based on the collected demographic and medical data, the established patient care plan guidelines, and goals to be achieved by the patient care plan, such as may be specified in the established patient care plan guidelines and/or patient medical data. These operations are performed by the patient health management system 410 utilizing the resources 418 which provide the rules, logic, equations, algorithms and other logic for evaluating patient information and correlating that information with a patient care plan that comprises patient actions to be performed by the patient and monitoring actions to be performed by the assessor. It should be appreciated that based on the demographic information about the patient and the patient's medical data, only a general patient care plan is generated at this point.

The resulting general patient care plan generated by the personalized care plan creation/update engine 414 is then personalized based on the lifestyle information for the patient obtained via the exogenous/lifestyle data analysis engine 413, to convert the general patient care plan to a personalized patient care plan for the specific patient based on their own unique combination of lifestyle information. The exogenous/lifestyle data analysis engine 413 obtains the lifestyle information from the various lifestyle information sources 424, 425 and performs analysis to generate lifestyle inferences from the lifestyle data. Again, resources may be provided in the resources storage 418 for providing logic, algorithms, rules, patterns, etc., for drawing these inferences from the received lifestyle information. For example, from schedule data for the patient, geospatial lifestyle information, environment lifestyle information, and the like for the patient, it may be determined, based on rules, patterns, algorithms, and the like, that the patient has a sedentary occupation, works in a multi-story building that has a gym, lives in an area with access to parks and walking paths, and the like. As one example, the lifestyle information may indicate that the patient's occupation is a lawyer. From that information, a lookup of the occupation in an occupation database provided in the resources 418 may indicate characteristics of the occupation including characteristics of "stressful", "sedentary", and "long hours" which provides lifestyle inferences about the patient that can be utilized by rules in the resources 418, implemented by the exogenous/lifestyle data analysis engine 413, to personalize the general patient actions in the general patient care plan to the particular patient. Various analysis of lifestyle information may be used to extract such inferences from the data which can then be used to personalize a general patient care plan via the personalized patient care plan creation/update engine 414.

As mentioned above, lifestyle information data is obtained from various sources 424, 425 to obtain an overall representation of the lifestyle of the patient. Third-party lifestyle information sources may provide lifestyle information that is combined with lifestyle information provided by the patient himself/herself for analysis to identify the types of personalized care plan actions to be used with the patient's care plan, the timing of the actions, and the types and timing of patient care plan monitoring and management actions to be performed by an assessor, e.g., a human assessor, automated assessment system, or a combination of human and automated assessment mechanisms. Thus, the selection of patient care plan actions (i.e. patient actions and monitoring actions) is based on the general patient care plan goals, the general patient care plan actions to be performed, and the personalization of these general patient care plan actions to the specific lifestyle of the patient.

Various lifestyle information analysis logic is provided in the exogenous/lifestyle data analysis engine 413 to evaluate and classify the patient's lifestyle in accordance with a number of defined lifestyle categories. For example, the patient's lifestyle may be categorized according to level of physical activity, level of availability to healthy food sources, quality of home and work environment (lighting, air quality, quietness, safety, etc.), level of access to exercise facilities, various qualitative aspects of the patient's home and work life, and the like. From these categories, a more specific patient care plan is generated to achieve the goals and actions of the generic patient care plan. Non-limiting examples of ways in which general patient care plans may be personalized based on lifestyle information have been provided above. Such personalization may be performed by the personalized care plan creation/update engine 414.

It should be appreciated that the resources 418 used by the patient health management system 410 may comprise various reference resources and logic (e.g., rules) from which the mechanisms of the patient health management system 410 may obtain information for making decisions as to how to personalize the patient care plan actions (patient actions and monitoring actions). Such reference resources may comprise drug information repositories, food nutrition repositories, exercise information repositories, medical procedure repositories, and the like. The "reference" resources differ from other information sources in that these "reference" resources tend to be universal for all patients. Such reference resources may be utilized, for example, to assist in determining drug affects on other lifestyle characteristics (e.g., drugs that make one lethargic, prone to disorientation, or the like), selecting foods whose nutritional content falls within the desired goals of a patient care plan, selecting exercises that generate a desired level of activity within a given period of time, and the like. Moreover, the resources 418 may further provide reference resources and rules/logic for evaluating exogenous information to identify exogenous conditions and associate these exogenous conditions with exogenous parameters specified in personalized patient care plans. For example, the resources may associate different levels of pollution, allergens, or the like, with specific categories of air quality which can then be used to evaluate against exogenous parameters of personalized patient care plans, e.g., patient A should have his/her personalized patient care plan modified if the air quality is determined to be "low".

It should be appreciated that in addition to the evaluation of the patient's demographic, medical, and lifestyle information, the personalized care plan creation/update engine 414 may evaluate the historical personalized care plan information for a patient and for other similar patients to determine appropriate patient actions to include in a personalized care plan. For example, the personalized care plan creation/update engine 414 may look to a history of personalized care plans created for this patient, as may be maintained in the personalized patient care plan database 416 in association with an identifier of the patient, to determine what patient actions the patient was able to successfully complete in previously prescribed personalized patient care plans and use this information to select those same patient actions for a current personalized patient care plan should the current personalized patient care plan have similar goals, general patient actions, and the like that the previously successful patient actions would satisfy. Thus, when selecting personalized patient actions to include in the personalized patient care plan, different weightings may be applied to patient actions based on whether or not they were previously prescribed to this patient, whether or not they were previously successfully completed by the patient in previously prescribed personalized patient care plans, and a level of successful or non-successful completion of the patient action in previously prescribed personalized patient care plans. A highest ranking patient action, amongst the possible patient actions, may then be selected for inclusion in the personalized patient care plan.

In addition, the personalized patient care plan creation/update engine 414 may retrieve information from the patient cohort database 417 to classify the patient into a patient cohort. The patient cohort is a grouping of patients that have similar characteristics, e.g., similar demographics, similar medical diagnoses, etc. Patient cohorts may be generated using any known or later developed grouping mechanism. One example mechanism may be using a clustering algorithm that clusters patients based on key characteristics of the patient, e.g., age, gender, race, medical diagnosis, etc. With regard to the illustrative embodiments, the present patient may be grouped into a patient cohort and the other members of the patient cohort may be evaluated to identify patient actions that the other members were able to successfully complete as part of their individual personalized patient care plans. These patient actions may then be provided for use in generating the personalized patient care plan for the present patient, with appropriate weightings applied to rank these patient actions relative to other patient actions for purposes of selection as discussed above.

Thus, the patient health management system 410 provides the various mechanisms for providing actual personalized patient care plans based not only on a categorization of the patient based on their medical diagnosis and demographic information, but also based on their own specific lifestyle information and lifestyle information obtained from third-party sources. In addition, the patient health management system 410 further provides the mechanisms for generating, as part of the personalized patient care plan, monitoring actions to be performed by an assessor in monitoring the patient's performance of the patient actions of the personalized patient care plan. That is, based on the creation of the series of patient actions to be performed by the patient over a designated period of time, e.g., daily, weekly, monthly, etc., corresponding monitoring actions are identified by the personalized care plan monitor engine 415 using the resources 418. The resources 418 may comprise rules, logic, patterns, algorithms, etc. that match monitoring actions to types of patient actions. Based on timing information for the patient actions, preferences specified by the patient in the patient supplied lifestyle information 421, and the like, these monitoring actions may be scheduled as part of the personalized patient care plan monitor, e.g., every day the patient wakes at 7:00 a.m. and eats breakfast at 7:30 a.m., therefore schedule a monitoring action at 7:25 a.m. to send a text message to the patient's communication device to inform the patient that they should eat bran flakes for breakfast on Monday, Wednesday, and Friday of the week. It should be appreciated that not every patient action needs to have a corresponding monitoring action and that monitoring actions may be schedule for only a subset of the patient actions which are determined to be of most value in assisting the patient with adherence to the personalized patient care plan.

Thus, the resulting personalized patient care plan comprises patient actions to be performed by the patient, and corresponding monitoring actions to be performed by the assessor. Having generated a personalized patient care plan (PCP) taking into account the patient's personal lifestyle, the patient health management system 410 outputs the personalized patient care plan 419 to the requestor system 440 for use by the patient 442 in performing the patient actions of the personalized patient care plan. In addition, as noted above, the personalized patient care plan 419 further comprises monitoring actions that are to be performed by an assessor via assessor systems 430, which may be a human being utilizing communications and/or computing equipment 432-436 to perform their monitoring actions, an automated system 436 that automatically performs monitoring actions, or a combination of human and automated systems. The personalized patient care plan 419 is output to the assessor system(s) 430 such that the assessor may utilize the monitoring actions in the personalized patient care plan 419 to monitor and evaluate the patient's performance of the patient actions.

In monitoring the patient 442 and the patient's adherence to the personalized patient care plan 419, the assessor system(s) 430 may obtain feedback information from various patient systems 441 including a health/activity monitor system 444, communication device(s) 446, online feedback system(s) 448, or the like. Examples of health/activity monitor system 444 include wearable devices, such as a FitBit™, iFit™ Fitness Tracker, pedometers, medical equipment with data connectivity to one or more networks via wired or wireless data communication links, or the like. Examples of communication device(s) 446 may include smart phones with applications for communication via data networks to log health and activity data for the patient 442, conventional phones through which a human or automated mechanism places calls to the patient 442, or the like. Examples of online feedback system(s) 448 include websites for tracking a patient's medical condition including online food logs, weight monitoring services, and other health and activity monitoring systems. Any systems that facilitate monitoring and/or communication with an assessor may be used as part of the patient system(s) 441 without departing from the spirit and scope of the illustrative embodiments.

Examples of monitoring actions performed by the assessor system(s) 430 may include interrogating the health/activity monitoring devices and/or applications executing on the communication devices 446 or online feedback system(s) 448 associated with the patient, and initiating a reminder communication to be sent to the patient's communication device 446 via the assessor communication device 434 to remind the patient 442 to perform an action in accordance with their personalized patient care plan 419, scheduling a doctor's appointment for the patient and informing them of the appointment, initiating a call to the patient's communication device 446 to discuss their progress, or any other action that a human or automated assessment system 436 may perform to assist with the monitoring of the patient's adherence to the patients' personalized patient care plan 419. Moreover, results of the monitoring may be returned to the patient health management system 410 for use in modifying the personalized patient care plan 419 based on the patient's determined level of adherence to the personalized patient care plan 419.

In response to monitoring results and feedback gathered by the assessor system(s) 430, and provided back to the patient health management system 410, the personalized care plan creation/update engine 414 may dynamically adjust or modify the personalized patient care plan 419 based on a determined level of adherence to the personalized patient care plan 419. That is, the patient's adherence to their personalized patient care plan 419 is monitored via the assessor system(s) 430 and the patient system(s) 441, and determinations are made as to whether the patient meets the goals set forth in the personalized patient care plan 419 and/or performs the patient actions in the personalized patient care plan 419. If the patient does not meet the requirements of one or more goals in the patient care plan 419, an alternative goal determination logic of the personalized care plan creation/update engine 414 is employed to determine an alternative goal that the patient is more likely to be able to accomplish. This determination may be made based on the patient's actual progress towards attaining the original goal, the importance and type of the goal to the overall personalized patient care plan, e.g., adjustments to medication may not be able to be made depending on the particular care plan, and a pre-determined inter-changeability of the goals. These determinations may be made in a similar manner as previously described above with regard to the original generation of the personalized patient care plan utilizing the resources 418 and the like, with the adherence feedback and monitoring data being used as additional lifestyle information for influencing the selection of patient actions and corresponding monitoring actions.

In some cases, one goal may be adjusted in one direction and another in a different direction so as to balance the patient's ability to achieve a missed goal with an alternative goal while maintaining overall results that are to be generated, e.g., physical activity goal may be reduced while dietary goals may be increased so that the balance achieves the same overall effect. In some illustrative embodiments, the determination of alternative patient actions for performing the alternative goals may be based on a historical analysis of patient actions in other patient care plans that the patient and/or similar patients in the patient's cohort have undergone. This historical analysis may identify other similar patient actions that achieved similar results to the patient actions that the patient is found to not be able to achieve in the patient's current personalized patient care plan. Such historical analysis may be performed in a similar manner as previously described above but with a focus on patient actions that were not achieved by the patient 442 in the PPCP 419.

As discussed above, in addition to generating the personalized patient care plan based on analysis of a patient's EMRs, demographics, lifestyle information, correlation with other similar patients via patient cohorts, application of patient care plan guidelines to the information obtained from such analysis, and application of rules, logic, patterns, and algorithms specified in various resources, the mechanisms of the illustrative embodiments may further modify or adjust a patient's personalized patient care plan based on one or more exogenous conditions that are determined to affect the patient's own specific personalized patient care plan, based on the patient's medical maladies. Various types of exogenous information may be obtained from the sources 421-423, 425 via information communication interfaces 411, which may comprise application programming interfaces (APIs) for pulling information from these sources or receiving pushed exogenous information from these sources 421-423, 425. The exogenous information obtained from these sources 421-423, 425 may be used in conjunction with the lifestyle information obtained from sources 424, 425, and the results of analysis of the patient's EMRs, demographics, and application of resources 418 and patient care plan guidelines 426 as discussed above to determine which exogenous factors in the exogenous information apply to the particular patient and the patient's personalized patient care plan. For example, GPS information from a lifestyle information source 424 may be used to determine the location of the patient to identify the particular portion of weather, pollution, and allergen information from sources 421-423 applies to the geographical location of the patient. This information may then be compared to the exogenous parameters or factors that affect the personalized patient care plan (PCP) for the patient as determined previously to determine if there are any changes needed.

That is, in some cases, based on the particular medical condition of the patient, the elements of the personalized PCP may be at least partially dependent, or affected, by one or more exogenous conditions, such as predicted or current weather, pollution, allergen levels, or other exogenous conditions. Such exogenous conditions are noted as part of the personalized PCP as exogenous parameters or factors to be monitored and potential triggers for dynamically modifying or adjusting the personalized PCP based on an evaluation of current or predicted exogenous conditions, as may be determined from exogenous information obtained from one or more exogenous information sources 421-423, 425. In some illustrative embodiments, these exogenous parameters or factors may be specified, for example, in terms of an exogenous factor or parameter identifier, a corresponding trigger value or threshold value, range of values, or the like, and a corresponding modification or adjustment action to be performed. It should be appreciated that multiple exogenous parameters/factors may be associated with a patient's personalized PCP and that each type of exogenous parameter/factor may have multiple different trigger values, threshold values, or ranges, with corresponding associated modification or adjustment actions to be performed.

For example, a patient's personalized PCP may indicate that a pollution levels are an exogenous parameter or factor that will affect the patient's personalized PCP and may indicate different levels of triggering values, threshold values, or ranges of values which may correspond to the Air Quality Index (AQI). For example, a first range of an AQI of 101 to 150 may be correlated to a moderate concern and a corresponding modification action of reducing strenuous outdoor activity in the patient's personalized PCP and a second range of 151 to 500 being correlated with a unhealthy or hazardous concern level and a corresponding modification action of eliminating all strenuous activity. The particular modification actions may be determined based on the information provided in patient care plan guidelines from source 426 and/or resources 418. The modification action may be applied to the corresponding elements of the personalized PCP to generate a modified personalized PCP. Modifications to such patient personalized PCPs may also result in changes to the assessor actions.

The exogenous/lifestyle data analysis engine 413 of the illustrative embodiments may monitor such exogenous conditions and update activities or actions to be performed by the patient and/or assessor in the personalized PCP based on the current or predicted exogenous conditions and the corresponding treatment guidelines for the particular medical conditions of the patient. The personalized PCP may be dynamically modified and the modified personalized PCP may be communicated to the patient via the requestor system 440 and/or directly with the patient systems 441. The modified personalized PCP may also be communicated to the assessor systems 430 for automatic modification of monitoring actions or notification to a human assessor.

Thus, the patient health management system 410 implements cognitive system logic via the demographic and medical data analysis engine 412 and exogenous/lifestyle data analysis engine 413 for analyzing the gathered information from the EMRs, demographic information, diagnosis information, lab test information, history information, medical guidelines and knowledge information, etc. and generates a personalized PCP for the specified patient including any conditional exogenous data parameters that need to be monitored and may trigger dynamic modification of the personalized PCP. The conditional exogenous data parameters to be monitored are specific to the medical conditions of the patient and may be identified based on the medical guidelines and knowledge from sources 426 and resources 418 as applied to the personal information about the patient as provided in the patient's EMRs and demographic information 420, diagnosis information, lab test information, history information, etc.

Based on the data from the exogenous information sources 421-423, 425, the exogenous/lifestyle data analysis engine 413 of the patient health management system 410 performs cognitive analysis to determine current and/or predicted exogenous conditions based on the received exogenous information from sources 421-423, 425. The personalized patient care plan creation/update engine 414 then analyzes each of the personalized PCPs of the patients that are being managed and determines which personalized PCPs are affected by the current and/or predicted exogenous conditions. Such a determination may be made based on the exogenous parameters for monitoring specified in the personalized PCPs and determining if a changed exogenous condition as determined through the analysis matches an exogenous parameter condition specified in the personalized PCP, e.g., specific allergen levels above a predetermined threshold, a pollution level above a specified threshold level, air quality index, or the like. For those personalized PCPs that are affected by the determined current and/or predicted exogenous conditions, the personalized patient care plan creation/update engine 414 modifies the personalized PCPs in accordance with medical guidelines and treatment knowledge from sources 426 and/or specified in resources 418 so as to avoid unnecessary risks to the patient's health. The modified personalized PCP may then be pushed to the patient's systems 441 and/or assessor systems 430 and appropriate notifications output to the patient and/or assessor indicating a change in the personalized PCP based on the current and/or predicted exogenous conditions. Such operations may be performed on a continuous or periodic basis, or in response to a triggering event, such as a patient or assessor request, e.g., directly or via requestor system 440, receipt of a pushed environmental condition warning from an official exogenous information source, e.g., environmental condition warning from a government website or exogenous information source in sources 421-423, 425, or the like.

For example, if the air quality index for the day is determined to be 153, the temperature is determined to be 87 degrees Fahrenheit, and allergen levels for tree pollen are determined to be high, the exogenous lifestyle data analysis engine 413 may analyze this combination of exogenous information and determine that an exogenous condition, parameter, or factor, of "environmental breathing difficulty" is of the level "very difficult." This exogenous parameter or factor may be specified as an exogenous parameter/factor affecting a personalized PCP for patient P who has asthma and allergies associated with tree pollens. The personalized PCP may indicate that if the "environmental breathing difficulty" exogenous factor is at a level of "difficulty" or above, then actions in the personalized PCP for patient P that are associated with strenuous outdoor activity should be modified to eliminate strenuous outdoor activity. This information may be used by the personalized patient care plan creation/update engine 414 to identify elements of the personalized PCP that are to be modified, i.e. elements having to do with strenuous outdoor activity, and may apply patterns, logic, rules, etc., from resources database 418 and patient care plan guidelines and knowledge from sources 426, to determine how to modify those elements in view of the modification specified by the correlation of the exogenous parameter or factor with a modification action. In this example, a strenuous outdoor activity element in the personalized PCP of patient P may comprise a walk along a specified outdoor path. This activity may be replaced by the personalized patient care plan creation/update engine 414 with a 30 minute walk on a treadmill at a local gym or in the home of the patient, i.e. indoor activity of a similar nature is used to replace the strenuous outdoor activity. In this way, a modified personalized PCP is generated for the patient dynamically based on the current or predicted exogenous conditions affecting the patient personally as indicated by the patient's personalized PCP.

It should be appreciated that the modified personalized PCP may be stored in conjunction with an identifier of the patient as a temporarily modified personalized PCP in the plan database 416. This temporarily modified personalized PCP is in effect until the patient health management system 410 determines that the current and/or predicted exogenous condition triggering the modification has subsided and the patient's health management may return to a normal state, e.g., new exogenous information from sources 421-423, 425 indicates another current or predicted change in the exogenous conditions that is different from the previously identified current/predicted exogenous condition. Thus, both the original personalized PCP and the modified personalized PCP may be stored in association with the patient in the plan database 416, with one being made active over the other depending on the particular exogenous conditions determined to currently exist or predicted to exist. In this way, multiple personalized PCPs may be generated that are keyed to different exogenous conditions and may be associated with different exogenous conditions such that if the exogenous condition occurs again in the future, the already stored modified personalized PCP in the plan database 416 may be automatically selected without having to rebuild the modified personalized PCP each time that the exogenous condition is determined to occur. Hence, multiple personalized PCPs for different exogenous conditions may be built up over time.

Thus, as described above, in addition to being able to generate personalized patient care plans for patients that take into account the patient's personal lifestyle information, the illustrative embodiments further provide mechanisms for dynamically modifying these personalized patient care plans based on current or predicted exogenous conditions that are determined to affect the patient's personalized patient care plan and potentially the health of the patient. Thus, on a dynamic basis the patient's personalized patient care plan may be adjusted to accommodate factors outside the patient's body that may affect the patient's health and treatment of their medical conditions so as to minimize risks to the patient and reduce issues that may unnecessarily exacerbate the patient's symptoms and medical maladies.

Figure 5:
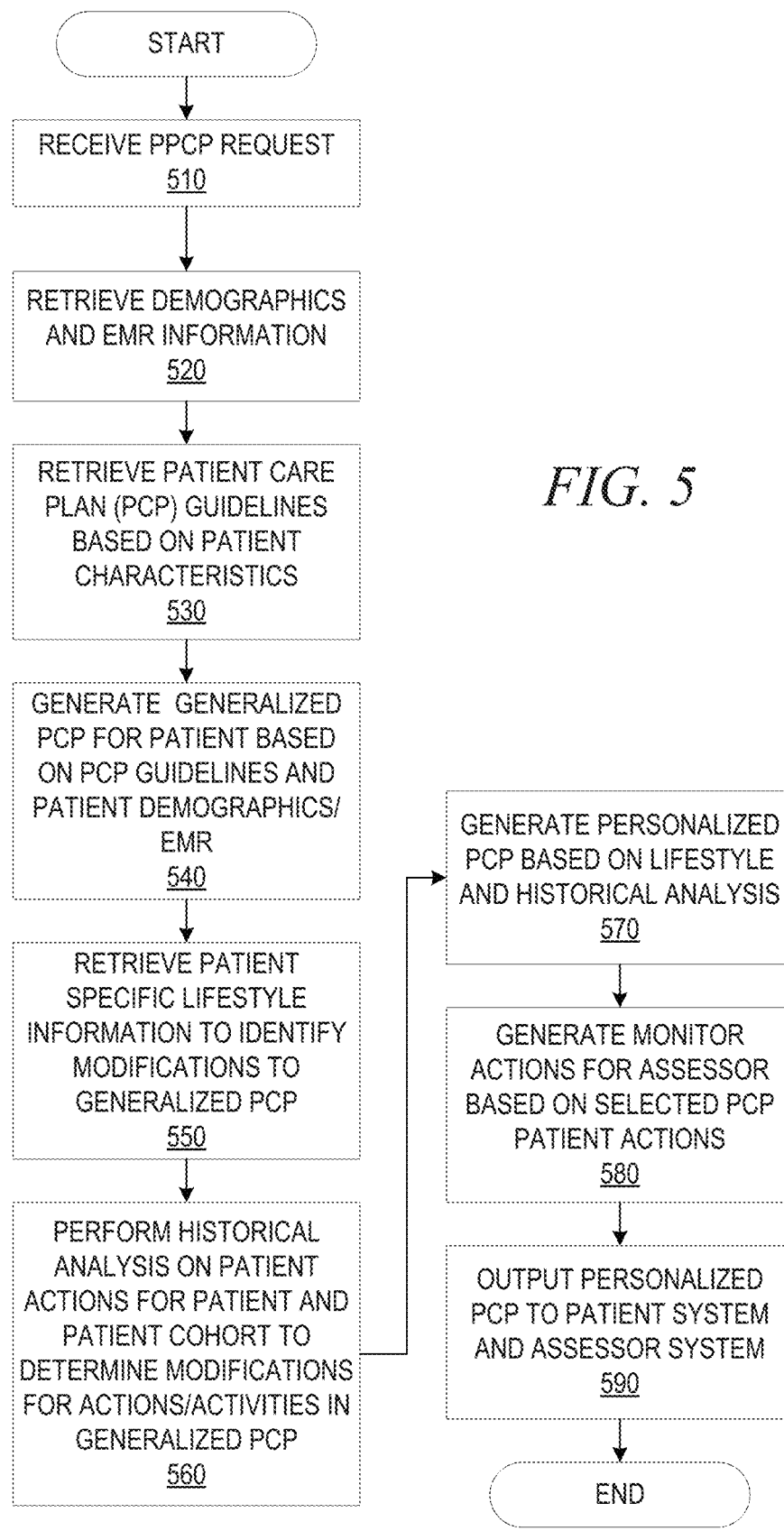
FIG. 5 is a flowchart outlining an example operation for creating a personalized patient care plan based on electronic medical records, patient information, and treatment guidelines in accordance with one illustrative embodiment.

FIG. 5 is a flowchart outlining an example operation for creating a personalized patient care plan in accordance with one illustrative embodiment. As shown in FIG. 5, the operation comprises receiving a request (Personalized Patient Care Plan (PPCP) request) for the creation of a personalized patient care plan specifically identifying a patient for which the personalized patient care plan is to be created (step 510). EMR and demographic information is retrieved for the patient (step 520) and used to retrieve one or more patient care plan guidelines corresponding to the patient's characteristics (step 530). A generalized patient care plan (PCP) is generated for the patient based on the retrieved PCP guidelines and the patient's demographics and medical information (step 540).

Patient specific lifestyle information is retrieved for the patient from a plurality of different lifestyle information sources (step 550). Moreover, in some illustrative embodiments, a historical analysis is performed on patient actions in previously prescribed PCPs for this patient and similar patients (such as patients in a same cohort) to identify patient actions that are ones that the patient is likely to be able to adhere to and weight them more heavily during a selection process (step 560). A personalized PCP is generated based on the generalized PCP as a basis which is then customized and personalized to the specific patient using the retrieved lifestyle information, the historical analysis results identifying patient actions that are likely to be adhered to by this patient, and established rules, patterns, algorithms, logic, etc., for generating personalized patient actions and combining them in a serial manner to generate a sequence of patient actions and goals that together constitute the patient's side of the personalized patient care plan (step 570). Based on the selected patient actions in the personalized patient care plan, corresponding monitor actions for all or a subset of the patient actions are generated using monitoring action rules, patterns, algorithms, logic, or the like (step 580). The monitoring actions are combined with the patient actions in the personalized PCP (PPCP) which is then output to the patient system(s) and assessor system(s) for implementation and monitoring of the PPCP (step 590). The operation then ends.

Figure 6:
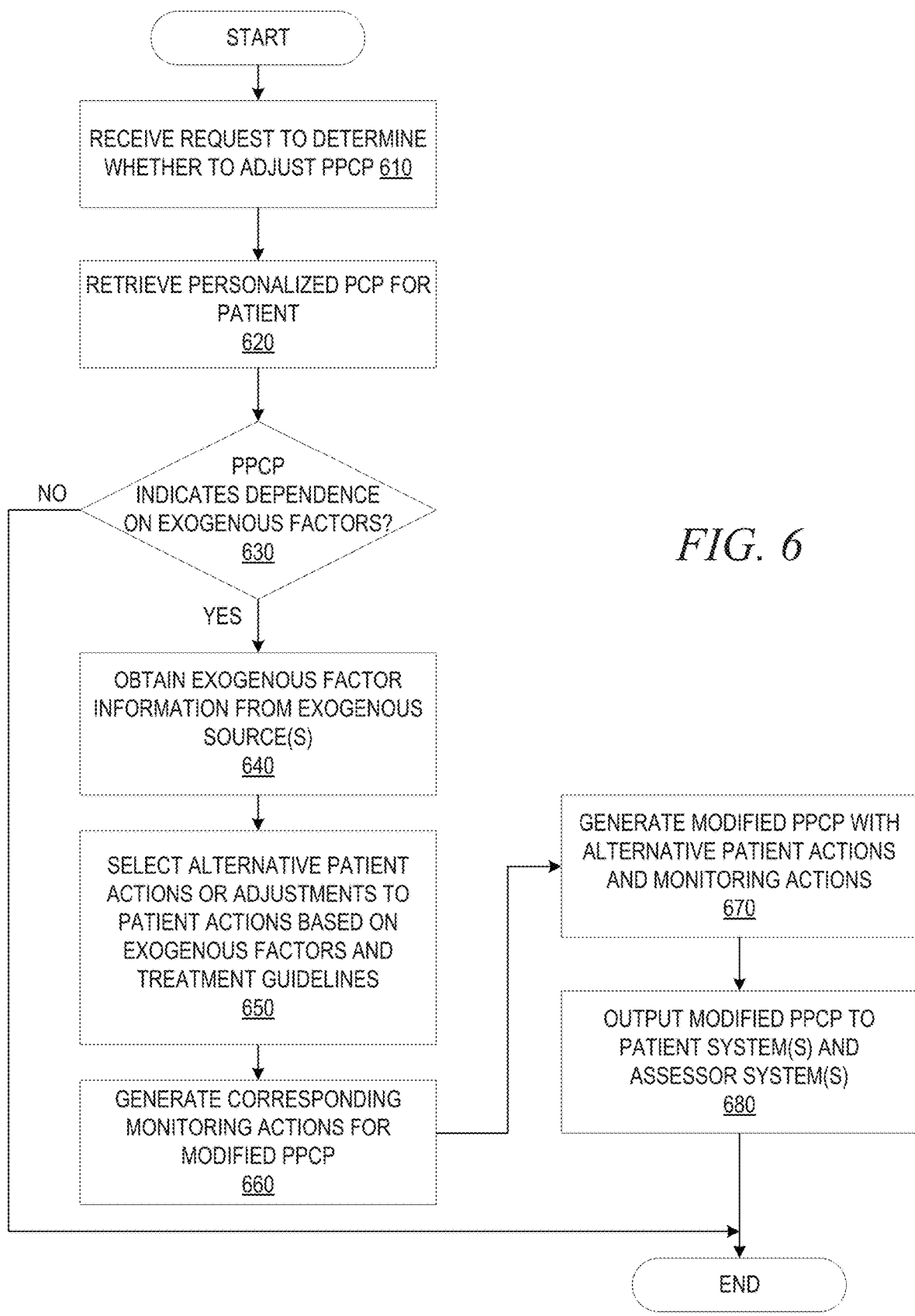
FIG. 6 is a flowchart outlining an example operation for adjusting a personalized patient care plan based on exogenous information from one or more exogenous information sources in accordance with one illustrative embodiment.

FIG. 6 is a flowchart outlining an example operation for adjusting a personalized patient care plan based on exogenous information from one or more exogenous information sources in accordance with one illustrative embodiment. As shown in FIG. 6, the operation starts by receiving a request to determine whether to adjust a PPCP of a patient based on exogenous conditions (step 610). The request may be automatically generated, such as on a periodic or continuous basis, may be provided by a user or in response to a trigger event, or any other condition that would cause a need to evaluate the PPCP of a patient with regard to exogenous conditions. As noted above, in some illustrative embodiments, this request may be automatically generated in response to new exogenous information being received from an exogenous information source indicating a new current or predicted exogenous condition that may affect patients.

The PPCP for the patient identified in the request is retrieved (step 620) and a determination is made as to whether the PPCP indicates any dependence on exogenous factors (step 630). For example, the PPCP may indicate particular types of exogenous conditions or factors that are to be monitored, e.g., air pollution levels, allergen levels, air quality index, temperature, etc., and corresponding trigger conditions, values, value ranges, etc. Moreover, the correlation of exogenous conditions or factors with triggering conditions/values may also be correlated with modification actions indicating types of PPCP elements that should be modified when the corresponding triggering conditions/values occur.

If there are no exogenous factors that would affect the PPCP, i.e. the PPCP is not indicated to be dependent on any exogenous factors in step 630, then the operation terminates. If there is at least one exogenous factor that would affect the PPCP, then the exogenous factor information is obtained from the exogenous information provided by one or more exogenous source(s) (step 640). Based on the correlation of exogenous factor values with information in the PPCP regarding exogenous factors to monitor and their associated triggering conditions/values and types of elements to modify based on the triggering conditions/values, as well as other information in guidelines, knowledge sources, resources, and the like, alternative patient actions or elements for adjusting the PPCP are selected for replacing existing elements of the PPCP (step 650). Corresponding monitoring actions are generated for modifications of the PPCP where appropriate (step 660). A modified PPCP is then generated based on the alternative patient actions or elements selected and the corresponding monitoring actions, if any (step 670). The modified PPCP is then output to patient system(s) and assessor system(s) (step 680). The operation then terminates.

Thus, the illustrative embodiments provide mechanisms for personalizing a patient care plan for a specific patient's own unique set of lifestyle characteristics such that the patient care plan is not generally applicable to a plurality of patients but is specific for the one patient. Information from various lifestyle information sources may be used along with patient care plan guidelines, demographic information, medical information, various resources, and the like, to generate a personalization of a more generic patient care plan that meets the desired goals for addressing a patient's medical condition. The personalization of the patient care plan may take into consideration patient actions that are successfully and unsuccessfully performed by the patient in other patient care plans, and by other similar patients with regard to their own personalized patient care plans. This may be done on a historical basis as well. Furthermore, the mechanisms of the illustrative embodiments provide monitoring actions for monitoring the patient's adherence to the personalized patient care plan and initiation of modifications to the personalized patient care plan when such adherence meets pre-defined criteria indicative of a need for a modification in the patient care plan. Moreover, the illustrative embodiments provide mechanisms for dynamically modifying or adjusting a personalized patient care plan in accordance with changing current or predicted exogenous conditions.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a patient health management system, wherein the patient health management system operates to perform the method comprising:

training a machine learning computer model of the patient health management system on training data comprising electronic medical record data of one or more patients and lifestyle data of the one or more patients, to generate a trained machine learning computer model;

analyzing, by the patient health management system executing in the data processing system, a patient electronic medical record (EMR) for an identified patient to identify a medical condition associated with the patient, wherein the patient EMR comprises clinical data associated with the patient obtained from one or more EMR data source computing systems;

generating, by a personalized patient care plan creation/update engine of the patient health management system, based on the identified medical condition, a personalized patient care plan data structure specifying a first personalized patient care plan for the patient comprising a plurality of patient actions to be performed by the patient to manage the medical condition, wherein the first personalized patient care plan is generated by executing, by the data processing system, the trained machine learning computer model of the patient health management system on the clinical data in the patient EMR and patient lifestyle information obtained from one or more patient lifestyle information source computing devices;

identifying, by the patient health management system, based on processing the first personalized patient care plan by the patient health management system, one or more exogenous data parameters associated with the first personalized patient care plan and correlating the one or more exogenous data parameters with one or more individual patient actions specified in the first personalized patient care plan, wherein the exogenous data parameters are parameters specifying conditions outside the patient's body that affect the health of the patient with regard to the medical condition;

retrieving, by one or more information communication interfaces of the patient health management system, exogenous data, corresponding to the exogenous data parameters, from one or more exogenous data sources;

determining, by an exogenous data analysis engine of the patient health management system, one or more modifications to one or more patient actions specified in the first personalized patient care plan based on processing the exogenous data by the exogenous data analysis engine; and generating, by the personalized patient care plan creation/update engine of the patient health management system, a second personalized patient care plan for the patient based on the determined one or more modifications to one or more patient actions at least by modifying at least one patient action to be performed by the patient in the first personalized patient care plan to be at least one modified patient action to be performed by the patient, that is different from the at least one patient action, wherein:

the at least one modified patient action minimizes effects of exogenous conditions, corresponding to the exogenous data parameters, on the health of the patient with regard to the medical condition, the second personalized patient care plan is stored in the personalized patient care plan data structure as a temporary alternative personalized patient care plan associated with an exogenous condition initiating the generating of the second personalized patient care plan, the personalized patient care plan data structure comprises a plurality of temporary alternative personalized patient care plans associated with the first personalized patient care plan, each temporary alternative personalized patient care plan being associated with a different exogenous condition, determining one or more modifications to one or more patient actions specified in the first personalized patient care plan based on the exogenous data further comprises retrieving, based on the exogenous data, a corresponding temporary alternative personalized patient care plan, from the plurality of temporary alternative personalized patient care plans of the personalized patient care plan data structure that corresponds to the exogenous condition, the original personalized patient care plan further comprises one or more assessor actions to be performed by an assessor via an assessor computing system for assessing compliance of the patient with the one or more patient actions, and generating the second personalized patient care plan further comprises generating one or more modified assessor actions corresponding to modified patient actions, and sending the one or more modified assessor actions to the assessor computing system for performance by the assessor in accordance with the second personalized patient care plan.

2. The method of claim 1, further comprising:

receiving updated exogenous data from the one or more exogenous data sources;

dynamically modifying one or more patient actions in the first personalized patient care plan based on the updated exogenous data to generate at least one other second personalized patient care plan associated with the updated exogenous data; and storing the at least one other second personalized patient care plan in the personalized patient care plan data structure for retrieval in response to subsequent receiving of same updated exogenous data.

3. The method of claim 2, wherein receiving updated exogenous data further comprises analyzing lifestyle information about the patient to identify portions of the updated exogenous data that affect the patient, and wherein dynamically modifying the one or more patient actions in the first personalized patient care plan comprises dynamically modifying the one or more patient actions in the first personalized patient care plan based on the portions of the updated exogenous data that affect the patient.

4. The method of claim 1, wherein generating the second personalized patient care plan comprises replacing a patient action in the first personalized patient care plan with an alternative patient action that minimizes effects of the exogenous condition on the patient.

5. The method of claim 1, further comprising generating and outputting a notification to at least one of the patient via a patient computing device, or a care manager via a care management system, indicating modifications to the one or more patient actions in the first personalized patient care plan.

6. The method of claim 1, wherein generating the first personalized patient care plan data structure further comprises, for one or more of the patient actions, generating and storing, in the personalized patient care plan data structure, in association with a corresponding patient action in the one or more patient actions, a corresponding exogenous parameter and a trigger condition of the exogenous parameter for triggering a modification of the corresponding patient action.

7. The method of claim 6, wherein the trigger condition comprises one or more ranges of values of the exogenous parameter or a threshold value of the exogenous parameter, and wherein generating and storing the corresponding exogenous parameter and trigger condition further comprises generating and storing, in the personalized patient care plan data structure, a corresponding identifier of a modification action to be performed on the corresponding patient action, in response to the corresponding trigger condition being met for the corresponding exogenous parameter.

8. The method of claim 1, wherein the second personalized patient care plan is used as a basis for measuring compliance of the patient with managing patient health until the patient health management system determines that exogenous conditions have changed to allow for restoration of the first personalized patient care plan.

9. A computer program product comprising a non-transitory computer readable medium having a computer readable program stored therein, wherein the computer readable program, when executed on a computing device, causes the computing device to implement a patient health management system which operates to:

train a machine learning computer model of the patient health management system on training data comprising electronic medical record data of one or more patients and lifestyle data of the one or more patients, to generate a trained machine learning computer model;

analyze, by the patient health management system executing in the data processing system, a patient electronic medical record (EMR) for an identified patient to identify a medical condition associated with the patient, wherein the patient EMR comprises clinical data associated with the patient obtained from one or more EMR data source computing systems;

generate, by a personalized patient care plan creation/update engine of the patient health management system, based on the identified medical condition, a personalized patient care plan data structure specifying a first personalized patient care plan for the patient comprising a plurality of patient actions to be performed by the patient to manage the medical condition, wherein the first personalized patient care plan is generated by executing, by the data processing system, the trained machine learning computer model of the patient health management system on the clinical data in the patient EMR and patient lifestyle information obtained from one or more patient lifestyle information source computing devices;

identify, by the patient health management system, based on processing the first personalized patient care plan by the patient health management system, one or more exogenous data parameters associated with the first personalized patient care plan and correlating the one or more exogenous data parameters with one or more individual patient actions specified in the first personalized patient care plan, wherein the exogenous data parameters are parameters specifying conditions outside the patient's body that affect the health of the patient with regard to the medical condition;

retrieve, by one or more information communication interfaces of the patient health management system, exogenous data, corresponding to the exogenous data parameters, from one or more exogenous data sources;

determine, by an exogeneous data analysis engine of the patient health management system, one or more modifications to one or more patient actions specified in the first personalized patient care plan based on processing the exogenous data by the exogenous data analysis engine; and generate, by the personalized patient care plan creation/update engine of the patient health management system, a second personalized patient care plan for the patient based on the determined one or more modifications to one or more patient actions at least by modifying at least one patient action to be performed by the patient in the first personalized patient care plan to be at least one modified patient action to be performed by the patient, that is different from the at least one patient action, wherein:

the at least one modified patient action minimizes effects of exogenous conditions, corresponding to the exogenous data parameters, on the health of the patient with regard to the medical condition, the second personalized patient care plan is stored in the personalized patient care plan data structure as a temporary alternative personalized patient care plan associated with an exogenous condition initiating the generating of the second personalized patient care plan, the personalized patient care plan data structure comprises a plurality of temporary alternative personalized patient care plans associated with the first personalized patient care plan, each temporary alternative personalized patient care plan being associated with a different exogenous condition, determining one or more modifications to one or more patient actions specified in the first personalized patient care plan based on the exogenous data further comprises retrieving, based on the exogenous data, a corresponding temporary alternative personalized patient care plan, from the plurality of temporary alternative personalized patient care plans of the personalized patient care plan data structure that corresponds to the exogenous condition, the original personalized patient care plan further comprises one or more assessor actions to be performed by an assessor via an assessor computing system for assessing compliance of the patient with the one or more patient actions, and generating the second personalized patient care plan further comprises generating one or more modified assessor actions corresponding to modified patient actions, and sending the one or more modified assessor actions to the assessor computing system for performance by the assessor in accordance with the second personalized patient care plan.

10. The computer program product of claim 9, wherein the computer readable program further causes the health management system to:
receive updated exogenous data from the one or more exogenous data sources;
dynamically modify one or more patient actions in the first personalized patient care plan based on the updated exogenous data to generate at least one other second personalized patient care plan associated with the updated exogenous data; and
store the at least one other second personalized patient care plan in the personalized patient care plan data structure for retrieval in response to subsequent receiving of same updated exogenous data.

11. The computer program product of claim 10, wherein the computer readable program further causes the health management system to receive updated exogenous data at least by analyzing lifestyle information about the patient to identify portions of the updated exogenous data that affect the patient, and wherein dynamically modifying the one or more patient actions in the first personalized patient care plan comprises dynamically modifying the one or more patient actions in the first personalized patient care plan based on the portions of the updated exogenous data that affect the patient.

12. The computer program product of claim 9, wherein the computer readable program further causes the health management system to generate the second personalized patient care plan at least by replacing a patient action in the first personalized patient care plan with an alternative patient action that minimizes effects of the exogenous condition on the patient.

13. The computer program product of claim 9, wherein the computer readable program further causes the health management system to generate and output a notification to at least one of the patient via a patient computing device, or a care manager via a care management system, indicating modifications to the one or more patient actions in the first personalized patient care plan.

14. The computer program product of claim 9, wherein the computer readable program further causes the health management system to generate the first personalized patient care plan data structure at least by, for one or more of the patient actions, generating and storing, in the personalized patient care plan data structure, in association with a corresponding patient action in the one or more patient actions, a corresponding exogenous parameter and a trigger condition of the exogenous parameter for triggering a modification of the corresponding patient action.

15. The computer program product of claim 14, wherein the trigger condition comprises one or more ranges of values of the exogenous parameter or a threshold value of the exogenous parameter, and wherein generating and storing the corresponding exogenous parameter and trigger condition further comprises generating and storing, in the personalized patient care plan data structure, a corresponding identifier of a modification action to be performed on the corresponding patient action, in response to the corresponding trigger condition being met for the corresponding exogenous parameter.

16. An apparatus comprising:
a processor; and
a memory coupled to the processor, wherein the memory comprises instructions which, when executed by the processor, cause the processor to implement a patient health management system which operates to:
train a machine learning computer model of the patient health management system on training data comprising electronic medical record data of one or more patients and lifestyle data of the one or more patients, to generate a trained machine learning computer model;
analyze, by the patient health management system executing in the data processing system, a patient electronic medical record (EMR) for an identified patient to identify a medical condition associated with the patient, wherein the patient EMR comprises clinical data associated with the patient obtained from one or more EMR data source computing systems;
generate, by a personalized patient care plan creation/ update engine of the patient health management system, based on the identified medical condition, a personalized patient care plan data structure specifying a first personalized patient care plan for the patient comprising a plurality of patient actions to be performed by the patient to manage the medical condition, wherein the first personalized patient care plan is generated by executing, by the data processing system, the trained machine learning computer model of the patient health management system on the clinical data in the patient EMR and patient lifestyle information obtained from one or more patient lifestyle information source computing devices;
identify, by the patient health management system, based on processing the first personalized patient care plan by the patient health management system, one or more exogenous data parameters associated with the first personalized patient care plan and correlating the one or more exogenous data parameters with one or more individual patient actions specified in the first personalized patient care plan, wherein the exogenous data parameters are parameters specifying conditions outside the patient's body that affect the health of the patient with regard to the medical condition;
retrieve, by one or more information communication interfaces of the patient health management system, exogenous data, corresponding to the exogenous data parameters, from one or more exogenous data sources;
determine, by an exogeneous data analysis engine of the patient health management system, one or more modifications to one or more patient actions specified in the first personalized patient care plan based on processing the exogenous data by the exogenous data analysis engine; and
generate, by the personalized patient care plan creation/ update engine of the patient health management system, a second personalized patient care plan for the patient based on the determined one or more modifications to one or more patient actions at least by modifying at least one patient action to be performed by the patient in the first personalized patient care plan to be at least one modified patient action to be performed by the patient, that is different from the at least one patient action, wherein:
the at least one modified patient action minimizes effects of exogenous conditions, corresponding to the exogenous data parameters, on the health of the patient with regard to the medical condition,
the second personalized patient care plan is stored in the personalized patient care plan data structure as a temporary alternative personalized patient care plan associated with an exogenous condition initiating the generating of the second personalized patient care plan, the personalized patient care plan data structure comprises a plurality of temporary alternative personalized patient care plans associated with the first personalized patient care plan, each temporary alternative personalized patient care plan being associated with a different exogenous condition, determining one or more modifications to one or more patient actions specified in the first personalized patient care plan based on the exogenous data further comprises retrieving, based on the exogenous data, a corresponding temporary alternative personalized patient care plan, from the plurality of temporary alternative personalized patient care plans of the personalized patient care plan data structure that corresponds to the exogenous condition, the original personalized patient care plan further comprises one or more assessor actions to be performed by an assessor via an assessor computing system for assessing compliance of the patient with the one or more patient actions, and generating the second personalized patient care plan further comprises generating one or more modified assessor actions corresponding to modified patient actions, and sending the one or more modified assessor actions to the assessor computing system for performance by the assessor in accordance with the second personalized patient care plan.

17. The apparatus of claim 16, wherein generating the first personalized patient care plan data structure further comprises, for one or more of the patient actions, generating and storing, in the personalized patient care plan data structure, in association with a corresponding patient action in the one or more patient actions, a corresponding exogenous parameter and a trigger condition of the exogenous parameter for triggering a modification of the corresponding patient action.

18. The apparatus of claim 17, wherein the trigger condition comprises one or more ranges of values of the exogenous parameter or a threshold value of the exogenous parameter, and wherein generating and storing the corresponding exogenous parameter and trigger condition further comprises generating and storing, in the personalized patient care plan data structure, a corresponding identifier of a modification action to be performed on the corresponding patient action, in response to the corresponding trigger condition being met for the corresponding exogenous parameter.

* * * * *